United States Patent
Nikitin et al.

(10) Patent No.: US 8,450,104 B2
(45) Date of Patent: May 28, 2013

(54) METHOD OF OPTICAL DETECTION OF BINDING OF A MATERIAL COMPONENT TO A SENSOR SUBSTANCE DUE TO A BIOLOGICAL, CHEMICAL OR PHYSICAL INTERACTION AND APPARATUS FOR ITS EMBODIMENT (VARIANTS)

(75) Inventors: Petr Ivanovich Nikitin, Moscow (RU); Boris Georgievich Gorshkov, Moscow (RU)

(73) Assignee: Petr Ivanovich Nikitin, Moscow (RU)

( * ) Notice: Subject to any disclaimer, the term of this patent is extended or adjusted under 35 U.S.C. 154(b) by 571 days.

(21) Appl. No.: 12/683,671

(22) Filed: Jan. 7, 2010

(65) Prior Publication Data
US 2010/0178207 A1      Jul. 15, 2010

Related U.S. Application Data

(62) Division of application No. 12/082,741, filed on Apr. 14, 2008, now Pat. No. 7,713,751, which is a division of application No. 10/275,929, filed as application No. PCT/RU01/00190 on May 10, 2001, now Pat. No. 7,368,294.

(30) Foreign Application Priority Data

May 11, 2000   (RU) ................. 2000111408

(51) Int. Cl.
*G01N 33/551*   (2006.01)
(52) U.S. Cl.
USPC ............. 435/288.7; 422/82.05; 422/82.11; 435/808
(58) Field of Classification Search
None
See application file for complete search history.

(56) References Cited

U.S. PATENT DOCUMENTS

| | | | |
|---|---|---|---|
| 3,970,389 A | | 7/1976 | Mendrin et al. |
| 4,190,366 A | | 2/1980 | Doyle |
| 4,558,012 A | | 12/1985 | Nygren et al. |
| 4,818,710 A | * | 4/1989 | Sutherland et al. ........... 436/527 |
| 4,820,649 A | | 4/1989 | Kawaguchi et al. |

(Continued)

FOREIGN PATENT DOCUMENTS

| | | |
|---|---|---|
| DE | 42 00 088 | 7/1993 |
| RU | 2141645 | 11/1999 |
| WO | 97/40366 | 10/1997 |

OTHER PUBLICATIONS

English translation of claims of DE 4200088 dated Jul. 15, 1993.

(Continued)

*Primary Examiner* — Chris L Chin
(74) *Attorney, Agent, or Firm* — Ladas & Parry LLP

(57) ABSTRACT

Apparatus for detecting biological or chemical components in liquid or gas is based on measuring changes of the sensor layer thickness due to binding reactions. A plate or a gap with two surfaces of a solid optical material is used as the sensor layer. The surfaces are located at a distance of more than 10 µm, which allows pumping liquids through the gap at moderate pressure drops and investigating large biological objects (e.g., cells), or employment of affordable plates that are rigid enough without any substrate. The indicated thickness of the plate or the gap permits using of the superluminescent diodes as light sources, because it allows recording within their narrow spectrum a sufficient number of interference maxima and minima for precise registration of molecular binding reactions, which lead to much higher sensitivity of the apparatus as compared with apparatus based on thin-film sensor layers.

17 Claims, 2 Drawing Sheets

U.S. PATENT DOCUMENTS

| | | |
|---|---|---|
| 5,124,172 A | 6/1992 | Burrell et al. |
| 5,132,097 A | 7/1992 | Van Deusen et al. |
| 5,561,069 A * | 10/1996 | Brigham-Burke et al. ... 436/518 |
| 5,680,214 A | 10/1997 | Lamb et al. |
| 5,815,278 A | 9/1998 | Johnston et al. |
| 5,872,629 A | 2/1999 | Colvard |
| 5,892,577 A | 4/1999 | Gordon |
| 5,999,262 A | 12/1999 | Dobschal et al. |
| 6,018,388 A | 1/2000 | Nawracala et al. |
| 6,111,644 A | 8/2000 | Ballard |
| 6,143,496 A | 11/2000 | Brown et al. |

OTHER PUBLICATIONS

English translation of RU 2141645 dated Nov. 20, 1999.
English translation of claims of WO 97/40366 dated Oct. 30, 1997.

* cited by examiner

METHOD OF OPTICAL DETECTION OF BINDING OF A MATERIAL COMPONENT TO A SENSOR SUBSTANCE DUE TO A BIOLOGICAL, CHEMICAL OR PHYSICAL INTERACTION AND APPARATUS FOR ITS EMBODIMENT (VARIANTS)

This application is a divisional of application Ser. No. 12/082,741 filed Apr. 14, 2008 now U.S. Pat. No. 7,713,751 which is a divisional of application Ser. No. 10/275,929 filed on Nov. 8, 2002 now U.S. Pat. No. 7,368,294 which is International Application RU01/0190 filed on May 10, 2001, which designated the U.S., claims the benefit thereof and incorporates the same by reference.

TECHNICAL FIELD

The proposed invention refers to the field of development of methods and tools for biological and chemical analyses.

BACKGROUND ART

An analogue of the proposed method [U.S. Pat. No. 4,558,012, Int. Cl. G01N 33/54, U.S. Cl. 436/501, 1985] is known that is intended for detection of chemical material components and measuring their concentration by detection of their binding to a sensor layer, which comprises:

irradiating of the sensor layer by light of various wavelengths, for which the sensor layer is transparent, at least, partially;

registration in the reflected light of a signal, which depends upon optical thickness of the said sensor layer and is due to the fact that interference on the said sensor layer modulates the reflection spectrum of the said sensor layer;

judging about the binding being detected from a change of the said signal.

In this method, the sensor layer is formed on a non-metallic substrate with high optical absorption, made preferably of a semiconductor, dark glass or plastic. The sensor layer consists of a number of transparent dielectric layers, a material that binds the chemical substance being detected, and the said chemical substance itself that forms a thin near-surface layer as a result of the said binding. The thickness of the sensor layer is chosen so that it acts as an antireflecting coating for polychromatic light of wavelengths within the range of (525-600) nm, which is incident to the said sensor layer. Interference on the sensor layer results in a reflection minimum in the said range. A change of the thickness of the sensor layer due to binding of the said chemical substance results in a spectral shift of the said minimum and, consequently, a change of color of the reflected light. This color change is registered visually and used for judging about presence or concentration of the chemical substance being detected.

Drawbacks of the analogue and the apparatus for its embodiment [U.S. Pat. No. 4,558,012, Int. Cl. G01N 33/54, U.S. Cl. 436/501, 1985] are its low sensitivity, not sufficient reliability and low precision of the results. This is due to qualitative, not quantitative, evaluation of the result and subjective character of the visual evaluation of the color change. Besides, these method and apparatus do not permit real-time registration of binding of chemical substances and investigation of kinetics of the process.

Another analogue [U.S. Pat. No. 4,820,649, Int. Cl. G01N 33/53, U.S. Cl. 436/501, 1989] of the proposed method is known that is intended for detecting components of biological systems, which comprises:

irradiating the sensor layer by light of various wavelengths, for which the sensor layer is transparent, at least, partially;

registration in the reflected light of a signal, which depends upon optical thickness of the said sensor layer and is due to the fact that interference on the said sensor layer modulates the reflection spectrum of the said sensor layer;

judging about the binding being detected from a change of the said signal.

The method of the analogue [U.S. Pat. No. 4,820,649, Int. Cl. G01N 33/53, U.S. Cl. 436/501, 1989] slightly differs from the method of the analogue [U.S. Pat. No. 4,558,012, Int. Cl. G01N 33/54, U.S. Cl. 436/501, 1985] in that it is applicable to substrates with high reflectivity, in particular, to metallic substrates. Matching the intensities of the light reflected from two boundary surfaces of the sensor layer, which is necessary for effective interference on the sensor layer and producing a clearly distinctive color, is achieved by employment of a semitransparent reflective film of small metallic particles. This metallic film is deposited onto the sensor layer after binding of the component being detected. This method and the apparatus for its embodiment [U.S. Pat. No. 4,820,649, Int. Cl. G01N 33/53, U.S. Cl. 436/501, 1989] have the same drawbacks as the method and apparatus [U.S. Pat. No. 4,558,012, Int. Cl. G01N 33/54, U.S. Cl. 436/501, 1985]. Moreover, they are also more complex and less reliable because of using of the said metallic film.

The closest to the proposed method is a method of optical detection of binding of at least one material component to a substance located on a surface of or inside the sensor layer on the basis of a biological, chemical or physical interaction [DE 42 00 088 C2, Int. Cl. G01N 21/45, 1997], which comprises:

irradiating the sensor layer by light of various wavelengths, for which the sensor layer is transparent, at least, partially;

registration in the reflected or transmitted light of a signal, which depends upon optical thickness of the said sensor layer and is due to the fact that interference on the said sensor layer modulates the reflection or transmission spectrum of the said sensor layer, respectively;

recording the spectrum of the said reflected or transmitted light as the said signal;

judging about the binding being detected from a change of the said signal.

According to this method, the sensor layer is located on a sufficiently transparent substrate and is irradiated by light of appropriate wavelengths from the side of the substrate. The sensor layer consists of, at least, partially, a layer of transparent inorganic (e.g. oxides, nitrides) or organic polymer (e.g. polystyrene) and a substance that implements the binding to be detected. The said substance is located on the surface of or inside the sensor layer and is capable to bind the said material component. Reaction of specific binding of an antibody with an antigen can be mentioned as an example of such binding. A material that enhances reflection is placed between the sensor layer and the substrate. The material forms one boundary surface of the sensor layer. The other surface is formed by an external medium. The external medium is commonly a biological solution under test, which contains or presumably contains the said component, whose binding is the object of detection.

Interference on the sensor layer results from combining of two or more secondary light waves produced as a result of partial reflection and partial transmission on the boundary surfaces of the sensor layer and, probably, on the interface surfaces inside the sensor layer. Said interference modulates the reflection and transmission spectra of the sensor layer. The spectrum of the reflected or transmitted light is recorded, and the absolute optical thickness of the sensor layer is determined from shape of the spectrum by analytical fitting. Information about a change of optical thickness of the sensor layer due to the binding being detected and, consequently, about parameters of the said binding is obtained from a change of the recorded spectrum.

Unlike analogues [U.S. Pat. No. 4,558,012, Int. Cl. G01N 33/54, U.S. Cl. 436/501, 1985] and [U.S. Pat. No. 4,820,649, Int. Cl. G01N 33/53, U.S. Cl. 436/501, 1989], the method-analogue [DE 42 00 088 C2, Int. Cl. G01N 21/45, 1997] provides capability of real-time detection of binding of material components to a substance of the sensor layer and detachment of the said components from the substance of the sensor layer, which is an important advantage of the method-analogue.

In the method-analogue, the sensor layer must be thin, i.e. there are a number of limitations implied on its thickness:
  the thickness is of the same order of magnitude as the wavelength of the used light;
  the double thickness is less than the coherence length of the used light;
  the thickness is within the range (0.3-10) μm, being not more than 5 μm in important practical cases and 2 μm in preferable variants.

The mentioned limitations are due to the principle of how the absolute thickness of the sensor layer is determined in the method-analogue. Employment of thicker sensor layers would result in interference pattern with many periods in the recorded spectrum. Unambiguous determination of the absolute thickness of the sensor layer from such interference pattern would be difficult or impossible.

The mentioned principle and related limitations on thickness of the sensor layer give rise to a number of drawbacks of the method-analogue. The spectral dependence of intensity of the reflected or transmitted light that serves for determination of the absolute optical thickness in the method-analogue represents a smooth curve that slowly varies within the observed spectral range. Due to this fact, any intensity variations in the recorded spectrum lead to significant errors in the measurement results. This particularly refers to variations that are non-uniform over spectrum. They can arise from drifts of operating parameters of the radiation source, changes of its temperature, heating of optical elements of the scheme, thermal and mechanical instabilities of the optical scheme due to changes of ambient conditions, etc.

Application of the method-analogue to multi-channel registration of structural changes of substances of the sensor layer including binding of material components to one or several substances of the sensor layer is known [U.S. Pat. No. 5,999,262, Int. Cl. G01B 9/02, U.S. Cl. 356/357, 1999]. In this method, the said structural changes in several spatially separated areas of the sensor layer are detected, and all the said areas are simultaneously irradiated by the light of the said wavelengths. The spectrum of the said reflected or transmitted light is recorded for each said area by using sequentially in time different wavelengths and implementing the following operations for each of the said wavelengths: irradiating the said areas by monochromatic light of one wavelength and measuring intensity of the said reflected or transmitted light for each said area.

As this takes place, the sensor layer is placed either on a plate-substrate, which is positioned on a base plate while measuring, or directly on the base plate. This is due to the fact that at the multi-channel registration [U.S. Pat. No. 5,999, 262, Int. Cl. G01B 9/02, U.S. Cl. 356/357, 1999] the sensor layer is also thin, and the same limitations as in the method-analogue [DE 42 00 088 C2, Int. Cl. G01N 21/45, 1997] are implied on its thickness.

The method of multi-channel registration is based on analysis of form of the recorded spectrum in each channel and, accordingly, determining of the absolute optical thickness of the sensor layer in each area. This means that the method-analogue [DE 42 00 088 C2, Int. Cl. G01N 21/45, 1997] is used for every channel (each area of the sensor layer under study). In this case, all the mentioned drawbacks of the method-analogue remain in its multi-channel variant. Moreover, they manifest themselves even stronger. Since in the method of multi-channel registration different spectral regions are recorded sequentially in time, any drifts and instabilities in intensity of the analyzed light in whole or in any region of its spectrum result in lower accuracy of measurements. Besides, as the multi-channel registration requires a powerful light source, the negative role of thermal instabilities of all elements of the optical scheme, namely: the source, detector, dispersion elements or spectral filters, assembly elements, etc. sharply increases. Such instabilities cause not only drifts of spectral distribution of the light intensity in each channel, but also drifts of intensity distribution of the analyzed light over the channels. Among characteristic examples, one can mention a change of color temperature of the light source due to heating of a filament and a change of intensity distribution of exposure along surface of the sensor layer and along surface of the photodetector, where images of different areas of the sensor layer are transformed, due to the filament sag because of heating. In these cases, uncontrollable drifts of both spectrum of the analyzed light and intensity distribution over the registration channels take place.

All this leads to low sensitivity, insufficient resolution, low reliability and precision of results obtained by the method-analogue [DE 42 00 088 C2, Int. Cl. G01N 21/45, 1997] and especially its multi-channel variant [U.S. Pat. No. 5,999,262, Int. Cl. G01B 9/02, U.S. Cl. 356/357, 1999]. Complexity, high labor input and cost can be mentioned among drawbacks of the method and, even more, its multi-channel variant.

Variants of the apparatus that realizes the proposed variants of the method are proposed.

The closest to the proposed apparatus is an apparatus-analogue intended for optical detection of binding of at least one material component to a substance located on a surface of or inside the sensor layer on the basis of a biological, chemical or physical interaction [DE 42 00 088 C2, Int. Cl. G01N 21/45, 1997], which comprises:
  a sensor layer;
  a source of light, which irradiates the sensor layer, of wavelengths that include at least operating wavelengths, for which the sensor layer is transparent, at least, partially;
  a detector, which is placed on the pathway of the light reflected from the sensor layer or transmitted through the sensor layer, for measuring the light intensity of operational wavelengths in the spectrum of the received light;
  a block of result generation, for example, a computer, to generate information about the binding being detected on the basis of changes of the said spectrum, whose input is connected to the output of the detector.

In the apparatus-analogue, the sensor layer is located on a transparent substrate, which is made preferably of glass, and the light from the source irradiates the sensor layer from the substrate's side. The sensor layer comprises a transparent, preferably inorganic, optical substance and a substance that binds a detected material component on the surface of or inside the sensor layer. A spectrometer preferably made on the basis of a photodiode array is used as a detector to register reflection or transmission spectrum of the sensor layer. The block of the result generation in the apparatus-prototype is made capable to determine the absolute thickness of the sensor layer from the recorded spectrum that is modulated by interference on the sensor layer.

As was discussed above during consideration of the method-analogue [DE 42 00 088 C2, Int. Cl. G01N 21/45, 1997], operation of the apparatus-analogue is based on the fact that binding being detected of material components on the surface of or inside the sensor layer changes optical thickness of the sensor layer. The block of result generation in specified moments of time determines the absolute optical thickness of the sensor layer from the spectrum recorded by a detector, and informs about the binding being detected based on a change of this absolute thickness.

The used in the apparatus-analogue principle of determining of absolute thickness imposes a number of simultaneous restrictions on thickness of the sensor layer:

thickness is of order of magnitude of the wavelength of the used light;
double thickness is less than the coherence length of the used light;
thickness is in the range (0.3-10) in practically important cases and preferable variants not exceeding 5 µm and 2 µm, respectively.

The mentioned peculiarities and restrictions of the apparatus-analogue give rise to a number of drawbacks discussed earlier while analyzing the corresponding method, namely, significant errors in measurement results due to uncontrollable intensity variations over the recorded spectrum or its intervals, low sensitivity and resolution, low precision and insufficient reliability of results of measurements.

A multi-channel variant of the apparatus-analogue is also known [U.S. Pat. No. 5,999,262, Int. Cl. G01B 9/02, U.S. Cl. 356/357, 1999], which is intended for investigation of structural changes, in particular, binding of material components, in several areas of the sensor layer. In the said apparatus, a source is monochromatic and tunable; the sensor layer is arranged either on a carrier plate or on a substrate placed on the carrier plate for measurements; the light irradiates simultaneously all the areas under study; a detector represents a set of photoelectric detectors; a control link is introduced between the block of result generation and the source to switch the latter to another wavelength of irradiated light after measurement by the detector of the intensity of received light for each said area at one wavelength; the block of the result generation is made capable to generate a spectral distribution of intensity of the received light over wavelength for each said area; judgment about binding being detected is made based on a change of the said spectral distribution for each said area.

Principle of operation of this apparatus consists in point-by-point determination of the spectrum for each area under study. At first, intensity in the spectrum is measured for all areas at one wavelength, then at another wavelength, etc. One determines absolute thickness of the sensor layer from the obtained spectra for each area and judges about binding being detected from a change of this thickness for each area.

A microtiter plate is also known [U.S. Pat. No. 6,018,388, Int. Cl. G01N 21/03, U.S. Cl. 356/246, 2000] for multi-channel registration of binding processes, which is a base component of the apparatus [U.S. Pat. No. 5,999,262, Int. Cl. G01B 9/02, U.S. Cl. 356/357, 1999]. In this plate, a sensor layer is up to 1 µm thick and formed on a bottom plate. There is at least one more layer between the sensor layer and the bottom plate. Back side of the bottom plate has an anti-reflecting coating. Areas of the sensor layer, for which the said binding is studied, are formed by a non-detachable joint of the bottom plate and a second plate that has a number of holes. The sensor layer in each area forms the bottom of a reaction cell while the holes of the second plate form side walls of these reaction cells.

Mentioned variants of the apparatus [U.S. Pat. No. 5,999, 262, Int. Cl. G01B 9/02, U.S. Cl. 356/357, 1999 and U.S. Pat. No. 6,018,388, Int. Cl. G01N 21/03, U.S. Cl. 356/246, 2000] employ the same principle of determination of thickness of the sensor layer as the apparatus-analogue [DE 42 00 088 C2, Int. Cl. G01N 21/45, 1997] and impose the same restrictions on the thickness of the sensor layer. As it was discussed above during analysis of the method [U.S. Pat. No. 5,999,262, Int. Cl. G01B 9/02, U.S. Cl. 356/357, 1999], all drawbacks of the apparatus-analogue [DE 42 00 088 C2, Int. Cl. G01N 21/45, 1997] are inherent to the apparatus [U.S. Pat. No. 5,999,262, Int. Cl. G01B 9/02, U.S. Cl. 356/357, 1999], including realization [U.S. Pat. No. 6,018,388, Int. Cl. G01N 21/03, U.S. Cl. 356/246, 2000], and they are even more pronounced.

Thus, the required technical result is to make measurement results independent from uncontrollable variations of intensity of the analyzed light in whole as well as in some parts of the spectrum and some regions of the sensor layer surface, and, consequently, to increase accuracy and reliability of the measurements, sensitivity and resolution with simultaneous reduction of a number of necessary operations, decreasing of labor-input and cost of the method and apparatus in both single- and multi-channel variants including real-time operation.

DISCLOSURE OF INVENTION

To achieve the said technical result the first variant of a method of optical detection of binding of at least one material component to a substance located on a surface of or inside a sensor layer due to a biological, chemical or physical interaction is proposed, which comprises:

irradiation of the sensor layer by light of various wavelengths, for which the sensor layer is transparent, at least, partially;
registration in the reflected or transmitted light of a signal, which depends upon optical thickness of the said sensor layer and is due to the fact that interference on the said sensor layer modulates the said reflection or transmission spectrum of the said sensor layer, respectively;
recording the spectrum of the said reflected or transmitted light as the said signal;
judging about the binding being detected from a change of the said signal,
which is similar to the method-analogue.

The proposed method is characterized in that:
thickness of the sensor layer exceeds 10 µm and, at the same time, exceeds the maximal wavelength of the said recorded spectrum by at least one order of magnitude;
the light, which irradiates the sensor layer, is collimated.

Besides, in the recorded spectrum at least two maximums or minimums due to the said interference are observed, and information about the binding being detected is obtained from a spectral shift of the said maximums or minimums.

Besides, monochromatic light is used as the light that irradiates the sensor layer, its wavelength being tuned.

Besides, polychromatic light is used as the light that irradiates the sensor layer.

Besides, polychromatic light with continuous spectrum and coherence length that is less than the double thickness of the sensor layer is used.

Besides, the sensor layer is placed on the substrate temporarily for the time of the said signal registration or permanently.

Besides, the light irradiates the sensor layer from the substrate's side, the substrate being transparent, at least, partially, for the said light.

Besides, a plate with surfaces not adjacent to any substrate is used as the sensor layer.

Besides, liquid being tested that contains or presumably contains a biological or chemical component, whose binding is the object of detection, is placed on one of the irradiated boundary surfaces of the sensor layer, while the other boundary surface is formed with using a substance that provides closeness of reflection coefficients of both boundary surfaces.

Besides, liquid is placed on both irradiated boundary surfaces of the sensor layer; the liquid being tested that contains or presumably contains a biological or chemical component, whose binding is the object of detection, is placed on at least one of the said boundary surfaces; liquid with the refractive index close to the refractive index of the liquid under test is arranged on the other surface.

Besides, the liquid being tested is placed on both said boundary surfaces and the said binding is detected from the side of both said boundary surfaces.

Besides, a layer of the liquid under test that contains or presumably contains a biological or chemical component, whose binding is the object of detection, is used as the sensor layer; the irradiated boundary surfaces of this layer are formed using hard optical materials; binding of the said component to at least one of the said boundary surfaces is detected.

Besides, binding of at least one material component in several spatially separated areas of the irradiated region of the sensor layer is detected; the spectrum of the said reflected or transmitted light is recorded for each said area; the said spectrum is used as the said signal for each said area.

Besides, the proposed method is characterized in that:
in each said area the sensor layer is formed by a plate with surfaces not adjacent to any substrate;
the spectrum of the said reflected or transmitted light for each said area is recorded by using sequentially in time different wavelengths of the light, which irradiate the sensor layer, and measuring the intensity of the said reflected or transmitted light for each said area at each wavelength.

Besides, the proposed method is characterized in that:
in each said area the sensor layer is formed by a layer of the liquid under test, which contains or presumably contains a biological or chemical component, whose binding is the object of detection; the irradiated boundary surfaces of the said layer are formed with using of hard optical materials; binding of the said component to at least one of the said boundary surfaces is detected;
the spectrum of the said reflected or transmitted light for each said area is recorded by using sequentially in time different wavelengths of light, which irradiate the sensor layer, and measuring the intensity of the said reflected or transmitted light for each said area at each wavelength.

Besides, polychromatic light is used as the light that irradiates the sensor layer; the spectrum of the said reflected or transmitted light for each said area is recorded by using sequentially in time light of different wavelengths; the intensity of the said reflected or transmitted light for each said area is measured for each said wavelength.

Besides, all the said areas are irradiated simultaneously.

Besides, several different substances capable to selectively bind various material components are placed in the said areas.

Besides, bindings of the various material components to the said different materials are detected.

Let us explain the proposed variant of the method and show that it is its distinctive features that ensure the required technical result.

In this variant of the method, obtained results are independent of uncontrollable variations of intensity of the analyzed light because of using the sensor layer with thickness that exceeds 10 µm and, at the same time, exceeds the maximal wavelength of the said recorded spectrum by at least one order of magnitude. Besides, the wavelength range of the light that irradiates the sensor layer is chosen rather wide; several maximums and minimums due to the interference on the sensor layer are observed in the recorded spectrum; judgment about the binding under test is made from a spectral shift of the said maximums and minimums. At least two said maximums and minimums are observed in the recorded spectrum while in preferred realizations of the method multiple (5-10 and more) intensity maximums and minimums are observed. The spectral position of the said maximums and minimums serve as the source of information about the binding being detected. Binding of material components to substances located on a surface of or inside the sensor layer leads to an increase of optical thickness of the sensor layer $d^*$, and, consequently, to a decrease of the period $\Delta v$ of the periodic interference pattern recorded in the frequency spectrum of the reflected or transmitted light, according to the relationship:

$$\Delta v = c/2d^* \qquad (1).$$

Here c is the speed of light in vacuum and $$d* = \int_0^d n(z)dz, \qquad (2)$$

where d is geometric thickness of the sensor layer, n(z) is the distribution of the refraction index of the sensor layer over its thickness.

It is easy to mention that the increase of optical thickness of the sensor layer results in a shift of the interference maximums and minimums in the spectrum of the reflected or transmitted light towards longer wavelengths. Accordingly, the opposite reaction of detachment of material components from substances of the sensor layer is accompanied by a decrease of optical thickness and to a shift of the interference maximums and minimums towards shorter wavelengths.

It is important to note that the light beam, which irradiates the sensor layer and whose spectrum is recorded, should be sufficiently collimated so that the difference of optical paths inside the sensor layer for different rays of the beam and all wavelengths of the recorded spectrum does not exceed approximately a fourth of light wavelength. Otherwise, at this wavelength an interference maximum for one ray overlaps an interference minimum of another ray, which causes diffusion of the interference pattern in the spectrum of the reflected or transmitted light. In multi-channel modifications of the method (see below), the said collimation level should be provided individually in each channel or in each area of the sensor layer, which is analyzed independently from other areas.

As the thickness of the sensor layer exceeds wavelengths of the recorded spectrum by one or more orders of magnitude, frequencies of the recorded spectrum significantly exceed the frequency period of the interference pattern $\Delta v$, and maximums or minimums corresponding to larger values of $\Delta v$ are observed in the recorded spectrum. Hence, it is spectral shift of the interference maximums and minimums that is first of all observed at a change of thickness of the sensor layer, and this shift is a much more pronounced effect that a change of distance between maximums or minimums in the recorded spectrum. When thickness of the sensor layer is sufficiently large as compared with operating wavelengths, the spectrum of operating wavelengths is wide enough, and at most common in practice low reflection coefficients of the boundary surfaces of the sensor layer the interference pattern in the recorded spectrum has many periods and can be considered with good accuracy as a sinusoid or, more precisely, a sinusoid modulated by spectrum of the affecting light. In this case, tracking of phase of the said sinusoid can be a convenient method to obtain an information signal. To take into account the modulated character of the sinusoid, it is convenient to apply the fast Fourier transformation to the recorded spectrum containing the interference pattern and to track the phase of the first harmonic.

Thus, in the proposed method the information signal is formed on the basis of registration of spectral position of individual interference maximums or minimums, or the whole interference pattern (a "comb" of interference maximums and minimums). Hence, contrasting to the known method [DE 42 00 088 C2, Int. Cl. G01N 21/45, 1997 and U.S. Pat. No. 5,999,262, Int. Cl. G01B 9/02, U.S. Cl. 356/357, 1999], variations of intensity of the analyzed light in whole or of different parts of the recoded spectrum do not affect the information signal, which ensures the required technical result.

The required technical result is also achieved in respect of simplification of the method, reduction of the number of necessary operations, decreasing of labor input and cost. Indeed, unlike the known method [DE 42 00 088 C2, Int. Cl. G01N 21/45, 1997 and U.S. Pat. No. 5,999,262, Int. Cl. G01B 9/02, U.S. Cl. 356/357, 1999], the proposed method does not require analytical fitting of regions of spectral dependences or getting information about absolute thickness of the sensor layer, although it is capable to do this. Generally speaking, the information about absolute thickness is excessive for registration of reactions of binding of biological and chemical components to substances of the sensor layer. For registration of reactions of binding and detachment it is sufficient to register changes of thickness, i.e. measure relative, not absolute, quantities. On one hand, this is much easier, on the other hand, provides much higher precision. It is the principle that is used in the proposed method.

One of the options to register the spectrum modulated by interference on the sensor layer is employment of monochromatic light as the light that irradiates the sensor layer; its wavelength is tuned on wavelengths, for which the sensor layer is transparent, at least, partially. In this case, registration of the spectrum is implemented in the simplest way, i.e. by measuring the intensity by, for example, a photodetector, and spectral distribution of the light intensity can be measured at a highest resolution on both intensity and wavelength. Thus, the required technical result is ensured. Besides, this realization of the method is good for registration of binding in a large number of different areas of the sensor layer simultaneously, i.e. for obtaining the required information in a large number of channels concurrently and independently from each other.

Other options of spectrum registration are in using of polychromatic light as the light that irradiates the sensor layer. These techniques are most appropriate for single-channel schemes or schemes with a small number of registration channels because of lower requirements to the radiation source, diminished number of operations, simplicity and lower cost. In these techniques, the spectrum of the reflected or transmitted light is recorded either entirely at a time, e.g. by an array spectrometer, or by measuring sequentially in time intensity of the light at one wavelength for a number of operating wavelengths. While affecting the sensor layer by polychromatic light it is reasonable to use the light with continuous spectrum and coherence length that is less than the double thickness of the sensor layer. The continuity of the spectrum is important for finding the spectral position of interference maximums or minimums with maximal accuracy, and the mentioned condition for the coherence length means that there are not less than two interference maximums or minimums of intensity of the transmitted or reflected light within the spectrum width of used polychromatic light. Importance of the latter condition was already mentioned above. Strictly speaking, a less strict limitation could be implied to obtain not less than two interference periods in the recorded spectrum. The coherence length that is less than the double optical, not geometric, thickness of the sensor layer would be a sufficient condition. It is known that the optical thickness always exceeds the geometric one. The mentioned limitation means that there are always more than two interference periods in the recorded spectrum.

It should be noted that in the proposed method the condition "the coherence length of the light that irradiates the sensor layer is less than the double thickness of the sensor layer" does not exclude interference or observation of the interference pattern in the recorded spectrum. This is easy to understand taking into account that recording of the spectrum of the reflected or transmitted light while affecting the sensor layer by polychromatic light is always done by extracting of narrow spectral intervals from the reflected or transmitted light near different wavelengths and registration of the light intensity within these intervals. The light extracted in each said spectral interval has the coherence length, which is much longer than that one of the original polychromatic light and, at the same time, larger than the double thickness of the sensor layer. The latter condition means that for each said extracted narrow spectral interval the result of interference on the sensor layer is observed in the recorded spectrum.

The proposed method allows for different options of formation of the sensor layer. At rather small thickness (tens of microns) the sensor layer is formed on a substrate to provide the necessary mechanical firmness and stability of the measuring scheme. It is rational also to use the substrate while working with replaceable samples of the sensor layer for reliable fixation of the said replaceable sample on the solid and firmly fixed substrate during a study of binding reactions in the sample. When the sensor layer is placed on the substrate temporarily for the time of registration of the said signal or permanently, it is preferable to irradiate the sensor layer by light from the substrate's side, the substrate being transparent, at least, partially, for the light. This increases accuracy of measurements and enlarges field of application of the method, providing a possibility of operation with absorbing or diffusing media being tested, which, in this case, are placed with respect to the sensor layer from the side that is opposite to the substrate.

Since in the proposed method upper limits for thickness of the sensor layer, which are inherent to the method-analogue and other analogues, are eliminated, there is an opportunity to employ a plate not adjacent to any substrate as the sensor layer. Fabrication of the sensor layer on the basis of a relatively thick plate (e.g. hundreds of microns) provides the necessary hardness of the sensor layer and stability of its characteristics without using of carrier or guide plates (substrates) and, hence, permits one to simplify the method and to reduce its cost. The plate that forms the sensor layer can be immersed in the medium under test (liquid or gas), from whose side the binding under investigation takes place. Another preferable variant is that the plate that forms the sensor layer serves as the bottom or a wall of a reaction cell, in which the medium under test (e.g. a biologically active solution) is placed.

In both cases, i.e. for the sensor layer located on a substrate or fabricated on the basis of a separate plate, the preferable realization of the method is that one, in which the liquid under test containing or presumably containing a biological or chemical component, whose binding is the object of detection (the subject of investigation), is placed on one of the irradiated boundary surfaces of the sensor layer while the other boundary surface is formed with using of a substance that provides closeness of reflection coefficients of both boundary surfaces. For example, the sensor layer forms the bottom or a wall of a reaction cell. Then when using a substrate, it is reasonable to form the other boundary surface of the sensor layer using an optically denser substance so that the reflectivity of the interface between this substance and the sensor layer is almost equal to the reflectivity of the interface between the sensor layer and the liquid under test. The said optically denser substance can be either the substance of the substrate or the substance of the layer specially introduced between the sensor layer and the substrate. In both cases, it is reasonable to use an antireflecting coating on the other, rear, surface of the substrate to suppress parasitic reflection. If the sensor layer is formed by a separate plate, whose one surface contacts the liquid under test and the other surface contacts the air, then it is reasonable to form an antireflecting coating on the other surface of the plate. While this takes place, in all described variants according to this embodiment, closeness of reflection coefficients of both boundary surfaces of the sensor layer is ensured. This allows one to reach the maximal contrast of the interference pattern in the spectrum of the reflected or transmitted light and, hence, the maximal ratio of useful signal to background signal. Thus, sensitivity of the method and precision of measurements increase.

If the sensor layer is formed by a separate plate not adjacent to any substrate, it is possible to use liquid on the second boundary surface to equalize reflection coefficients of both boundary surfaces. For this, liquids are placed on both irradiated boundary surfaces of the sensor layer; the liquid under test that contains or presumably contains a biological or chemical component, whose binding is the object of detection, being placed on at least one of these boundary surfaces. In the simplest and most preferable realizations, when refractive indices of materials near both boundary surfaces of the sensor layer are equal, the liquids on both boundary surfaces should have the same refractive index. For example, it may be the same liquid under test. This opportunity can be realized by a special design of a flow cell, in which the liquid under test flows on both sides of the plate—sensor layer, or by simple immersion of the plate—sensor layer into a reservoir with the liquid under test. The most preferable realization is that, in which the liquid under test is placed on both boundary surfaces and the said binding is detected from both said boundary surfaces. Such realization of the method doubles a change of the optical thickness of the sensor layer and, hence, doubles sensitivity and resolution of the method while analyzing the liquid under test for presence of any biological or chemical components.

The proposed method opens a number of new possibilities, when a layer of the liquid under test, which contains or presumably contains a biological or chemical component, whose binding is the object of detection, is used as the sensor layer; the irradiated boundary surfaces of the said layer are formed with using of hard optical materials; and binding of the said component to at least one of the said boundary surfaces is detected. In particular, fabrication of the sensor layer is significantly simplified and, respectively, the whole method becomes much simpler and more cost-effective. Instead of deposition of the sensor layer onto a substrate or its fabrication as a plate, in this case it is sufficient to position two prepared flat surfaces of optical blocks so that they face each other, fix the distance between them by an insertion of appropriate thickness, and introduce the liquid under test into the gap. Obviously, at registration of the information signal in the transmitted light the optical materials on both sides of the layer of the liquid under test should be sufficiently transparent, while at registration of the information signal in the reflected light transparency of only that optical block, from which the light is incident to the layer, is sufficient. An important circumstance is that the insertion material can be chosen so that its thermal extension at temperature drifts corresponds to a decrease of the refractive index of the liquid under test. In such a way, uncontrollable changes of optical thickness of the sensor layer due to temperature drifts are compensated. Only the changes of optical thickness are registered, which are due to binding components from the liquid under test to the substances (e.g. specifically binding substances, bio-receptors, etc.) located on the said prepared surfaces of the optical blocks. As a result, measurement errors significantly decrease, the accuracy and reliability of the results increase.

It should be noted that both variants of the proposed method, discussed below, apply also to detection of binding components of not only liquid components as discussed above, but also to gases. Liquids under test in the proposed method are solutions (including colloid mixtures, suspensions, etc.) that contain biological or chemical components, which, as a rule, are biologically active. Among such biological components different antigens and antibodies, proteins, viruses, their fragments and antigen determinants, bacteria, nucleic acids, their fragments and nucleotide sequences, lipids, polysaccharides, carbohydrates, enzymes, hormones, etc., and also receptors specific to these components. In the proposed method, binding of such components to substances located on a surface of or inside an optically transparent sensor layer is registered. These substances can be optical substances that form boundary surfaces of the sensor layer or receptors for binding components being detected, which are immobilized on these surfaces. Besides, the binding can take place inside the sensor layer, for example, inside a three-dimensional biomolecular array (polymer long-chain molecules, dextrain, polypeptides, etc.) or in pores inside the sensor layer, where correspondent receptors can be also immobilized. Similarly, the sensor layer can adsorb or absorb detected components of gaseous mixtures on its surface or inside, for example, in its pores, including using of specifically sensitive substances (e.g. phthalocyanines for nitric oxide, etc.). As a result of binding of gaseous components and vapors, the sensor layer can also change the thickness (in particular, swell) or the refractive index, or spectral characteristics of transmission/reflection (color), etc. Appropriate substances for the sensor layers capable to bind biological and chemical components are known from state of the art of biochemical and gas analyses.

The proposed method applies also to registration of binding of components on several or multiple channels, data for each registration channel being received independently of data from the other channels. The data are received for all the channels either simultaneously (parallel mode) or the channels are interrogated in sequence (serial mode). In some cases, groups of channels are interrogated in sequence (lineby-line mode). Combinations of the mentioned modes are also possible. In multi-channel modifications of the first variant of the proposed method binding of at least one component in several spatially separated areas of the irradiated region of the sensor layer is detected; the spectrum of the said reflected or transmitted light for each said area is recorded; this spectrum is used as the said signal for each said area. In one registration channel either a single area is used, for which one receives a separate information signal (in this case, the spectrum), or a group of areas, in which equal conditions are created for binding components being detected. For example, one registration channel can be realized on the basis of one reaction cell, in which a receptor substance for binding a definite component is immobilized. This channel corresponds to one said area when an information signal is registered from this cell as a whole, or to several areas, if independent information signals are obtained from different areas of the cell (e.g. if the light transmitted or reflected from the cell is incident simultaneously on several photodetecting zones with independent outputs). To increase accuracy of measurements and reliability of results in the latter case it is reasonable to average the information signals over several areas within one reaction cell and use the obtained result as an information output of this registration channel. However, one can also consider each area that corresponds to a separate photodetecting zone and separate information output as forming a separate registration channel.

The said areas can be regions of surface of either a one-piece sensor layer or a sensor layer that consists of separate pieces. In the latter case, these pieces can be significantly spatially separated and even have different orientation of surface, e.g. if the sensor layer consists of a number of regions with fiber-optical inputs and outputs. It is only necessary that each said area is irradiated by light and detection of a separate independent information signal is provided for each area. For this, it is sufficient that no said area overlaps the light incident to another area. Each said area comprises parts of both boundary surfaces and of volume of the sensor layer, which are irradiated by the same light beams, including cases, when binding of components from both boundary surfaces' side or inside the sensor layer is studied.

Multi-channel modifications of the proposed method are extremely important and provide the said technical result for a number of practically important purposes. First of all, independent registration of the information signal from several channels permits using channels to form a reference signal (reference channels) for different purposes. For example, it is reasonable to use the reference channels to compensate possible accidental errors, parameters' spread and non-uniformity of samples containing or presumably containing the components being bound.

In addition, the reference channels are applied to investigate specificity of binding of biological or chemical components to the receptors located on the surface of or inside the sensor layer. For example, for quantitative analysis of a solution for presence of a biologically active component (infectious or toxic agent, antigen or antibody, etc.), a reagent capable to selectively bind (recognize) the component under study is immobilized on the surface of the sensor layer or inside it (e.g. in a three-dimensional biomolecular array). Presence of this component in the solution is determined on the basis of the obtained data about its specific binding with the recognition reagent. To allow for non-specific (non-selective) binding of this or other components with the surface or volume of the sensor layer the reference channels are used.

Besides, during analyses that repeat in time or continuous monitoring the reference channels can serve to take account of temperature drifts as well as other physical or chemical instabilities (e.g. pressure, density, pH of the solution or concentration of parasitic additions, etc.).

In all these tasks, as a rule, the reference channel is in the same conditions as the information channel except conditions for selective binding of the component under study to the recognition reagent.

Employment of the reference channels lowers the registration threshold, increases reliability and accuracy of measurements and, thus, provides the required technical result.

Another group of tasks, where multi-channel registration is required, is provision of high throughput screening of the analyses. This is particularly important, for example, for testing new pharmaceutical products, when a huge number of tests are carried out to check interaction of the product with different reagents. For such tasks, in particular, a realization of the proposed method with the number of channels in accordance with modern standards of immunoassays (e.g. immuno-ferment assay "ELISA"—Enzyme-Linked Immuno-Sorbent Assay) is reasonable. In this case, the channels correspond to reaction cells of standard microtiter plates that contain, for example, 96 (12×8 array), 384 (24×16 array), 1536 (48×32 array) cells. The proposed method permits investigation of binding of biological and chemical components (e.g. with different components being bound and/or different binding reagents) simultaneously (in parallel) in a large number of channels corresponding to the said spatially separated areas of the sensor layer. This strongly increases the productivity of the method, decreases its cost, providing the said technical result.

The third group of tasks resolved with the multi-channel registration is recognition of complex multi-component mixtures and analysis of presence in them of simultaneously several components. It is discussed below.

One of the most preferable realizations of the multi-channel modification of the first variant of the proposed method is that in each said area the sensor layer is formed by a plate with surfaces not adjacent to any substrate; the spectrum of the said reflected or transmitted light for each said area is recorded by using sequentially in time different wavelengths, which irradiate the sensor layer; intensity of the said reflected or transmitted light for each said area is measured at each of these wavelengths. Scanning the wavelength of the light that affects the areas of the sensor layer provides the simplest way to register the said spectrum for each said area. This is because in this case analysis of the reflected or transmitted light represents measuring intensity of the light in each moment of time only at one wavelength, the spectrum wavelengths being sequentially changed. Independence of the measurements of intensity for each area is realized by projection of light from different areas onto different photodetector zones with independent outputs, which form a photodetector array, e.g. a CCD-array or a camcorder. To do this, an image of areas of the sensor layer is formed on the photodetector array or these areas are simply projected onto the said array by used collimated light. As a rule, the photodetector array is smaller than the set of areas under study, so optical systems are applied to form an image of smaller size or to project a collimated light beam of a reduced diameter, which is reflected from the said areas of the sensor layer or transmitted through them.

In this case, fabrication of the sensor layer as a plate not adjacent to any substrate realizes the method in the simplest way. It is convenient to form on this plate reaction cells correspondent to different registration channels by, for example, usual deposition (from solutions or by sputtering) of recognition reagents on different regions of the plate, by etching wells, by gluing masks with holes, gluing or welding this plate with another plate, in which holes form the reaction cells, or by other methods.

The multi-channel method is also realized in a very simple way, when in each said area the sensor layer is formed by a layer of the liquid under test containing or presumably containing a biological or chemical component, whose binding is the object of detection; the boundary surfaces of this layer exposed to the light are formed with hard optical materials; binding of the said component to at least one of the said boundary surfaces is detected; the spectrum of the said reflected or transmitted light for each said area is recorded by using sequentially in time different wavelengths, which irradiate the sensor layer; intensity of the said reflected or transmitted light for each said area is measured at each of these wavelengths. This case is similar to the previous one with the only difference that reaction cells are formed by holes in an insertion between two optical blocks restraining the layer of the liquid under test (see comments above).

Another realization of the method consists in that polychromatic light of wavelengths, for which the sensor layer is sufficiently transparent, irradiates separated areas of the sensor layer. That is, the said areas are exposed to the polychromatic light; the spectrum of the said reflected or transmitted light is recorded for each said area; the recorded spectrum is used as the said signal for each said area. In particular, at a small number of channels, each channel can be equipped by an array spectrometer. This significantly decreases the number of necessary operations and time consumption, makes the method simpler, lowers its cost and, in the same time, increases reliability of obtained data, which provides the said technical result. Another possibility that is preferable for a large number of channels consists in that polychromatic light is used as the light that irradiates the sensor layer; for each said area the spectrum of the said reflected or transmitted light is recorded by using sequentially in time different wavelengths; the intensity of the said reflected or transmitted light for each said area is measured at each of these wavelengths. For example, the light near one wavelength is extracted from the transmitted or reflected light by a dispersion element (a monochromator) or a spectral filter; at the said wavelength one registers an image of the said areas of the sensor layer on an array photodetector or representation of the said areas produced on the array photodetector by collimated light. By scanning the wavelength, the intensity distribution over wavelengths, i.e. the spectrum, is obtained for each area.

In realization of multi-channel modifications of the proposed method, it is preferable to affect by light simultaneously all areas of the sensor layer, in which binding of the components is investigated. This permits one to avoid scanning by light over the sensor layer surface, diminish the number of operations and time consumption, simplify the method and decrease its cost, increase reliability of obtained data and accuracy of measurements, providing the said technical result. In addition, this makes possible simultaneous (parallel) registration in many channels and, thus, increases temporal resolution of the method. This is important for observation of binding components in real time and investigation kinetics of this process.

All discussed multi-channel modifications of the proposed method allow one to effectively recognize complex multi-component mixtures and determine presence in them of simultaneously several components.

For this, several different substances capable to selectively bind (i.e. recognize) diverse material components are arranged on the said spatially separated areas of the irradiated region of the sensor layer. This engineering solution is rational also for investigation of interaction of one given component (e.g. new medicament) with a large number of different recognition substances simultaneously. Besides, binding of diverse material components to the said different substances is detected. In the simplest case, when selectivity of binding of each component with correspondent recognition reagent is sufficiently high, not more than one reagent and not more than one component under study correspond to each said area, i.e. one area "is responsible" for recognition of one component, some areas being used as reference channels. In other cases, a complex pattern of signals is obtained from the said areas, each signal possessing low specificity to an individual component, but the whole pattern proves to be selective (similarly to a fingerprint) with respect to the whole mixture under test. A mixture can be recognized, for example, by using computer methods of pattern recognition. Such modifications of the proposed method can be used for design of "biochips", "gene chips", electronic "nose" and "tongue", etc.

Capability to recognize simultaneously several components in biological or chemical media and complex mixtures under test extends the field of application of the method. Besides, this diminishes consumption of time and resources to carry out analyses, providing the said technical result.

It should be noted that the proposed method provides capability of real-time registration and investigation of processes of binding (detaching) of components. This concerns also modifications of the method, which include scanning over spectrum (sequential using of different wavelengths) of the affecting and either the reflected or transmitted light, because the characteristic time of binding reactions is usually sufficiently long (minutes and tens of minutes) and exceeds the scanning time. Certainly, the proposed method permits detection of results of already completed reactions of binding (detaching) of components regardless the characteristic time of such reactions.

The second variant of the method of optical detection of binding of at least one material component to a substance located on a surface of or inside a sensor layer due to a biological, chemical or physical interaction is also proposed, which comprises:

irradiation of, the sensor layer by light of various wavelengths, for which the sensor layer is transparent, at least, partially;

registration in the reflected or transmitted light of a signal, which depends upon optical thickness of the said sensor layer and is due to the fact that interference on the said sensor layer modulates the said reflection or transmission spectrum of the said sensor layer, respectively;

judging about the binding being detected from a change of the said signal, which is similar to the method-analogue.

The proposed method is characterized in that:

on the pathway of the light from the source to the detector a scanned Fabry-Perot interferometer is placed along with the sensor layer;

the base (i.e. optical path between the mirrors) of the scanned Fabry-Perot interferometer is chosen sufficiently large so that the period of the transmission spectrum of the said scanned Fabry-Perot interferometer is at least twice smaller than the width of spectral range of wavelengths participating in formation of the recorded signal;

the base of the said scanned Fabry-Perot interferometer is modulated;

distribution of intensity of the said reflected or transmitted light, summed up over the said spectral interval, as a function of base of the scanned Fabry-Perot interferometer is registered as the said signal.

Besides, collimated light is used as the light that irradiates the sensor layer and the scanned Fabry-Perot interferometer.

Besides, polychromatic light with continuous spectrum is used as the light that irradiates the sensor layer, the coherence length of the said polychromatic light and of the said reflected or transmitted light being less than the double base of the scanned Fabry-Perot interferometer.

Besides, polychromatic light of the coherence length that is less than the double thickness of the sensor layer is used.

Besides, at least one intensity maximum due to correlation between spectral characteristics of interaction of the light with the sensor layer and the scanned Fabry-Perot interferometer is registered in the said distribution. Judgment about the binding to be detected is made from a change of position of the said, at least one, maximum with respect to values of base of the scanned Fabry-Perot interferometer.

Besides, the scanned Fabry-Perot interferometer is placed on the pathway of the light, in which the said signal is registered, before its incidence onto the sensor layer.

Besides, the scanned Fabry-Perot interferometer is placed on the pathway of the said reflected or transmitted light, in which the said signal is registered, after reflection from the sensor layer or transmission through the sensor layer, respectively.

Besides, the scanned Fabry-Perot interferometer is used in the reflection mode.

Besides, the scanned Fabry-Perot interferometer is used in the transmission mode.

Besides, the sensor layer is placed on a substrate temporarily while registration of the said signal or permanently.

Besides, the sensor layer is irradiated by light from the substrate's side, the substrate being transparent, at least, partially, for this light.

Besides, a plate with surfaces not adjacent to any substrate is used as the sensor layer.

Besides, the liquid under test that contains or presumably contains a biological or chemical component, whose binding is the object of detection, is placed on one of the irradiated boundary surfaces of the sensor layer; the other boundary surface is formed with using of a material that provides closeness of the reflection coefficients of both boundary surfaces; liquid with the refractive index close to the refractive index of the liquid under test is arranged on the other surface.

Besides, liquid is placed on both irradiated boundary surfaces of the sensor layer; the liquid under test that contains or presumably contains a biological or chemical component, whose binding is the object of detection, being placed on at least one of these boundary surfaces; the other boundary surface is formed with using of a material that provides closeness of the reflection coefficients of both boundary surfaces.

Besides, the liquid under test is placed on both said boundary surfaces, and the said binding from the side of both said boundary surfaces is detected.

Besides, a layer of the liquid under test that contains or presumably contains a biological or chemical component, whose binding is the object of detection, is used as the sensor layer. The irradiated boundary surfaces of this layer are formed with using of hard optical materials; binding of the said component to at least one of the said boundary surfaces is detected.

Besides, binding of at least one material component is detected in several spatially separated areas of the irradiated region of the sensor layer; the said distribution is registered for each said area and used as the said signal for each said area.

Besides, the said distribution is registered for each said area by using sequentially in time of different values of base of the scanned Fabry-Perot interferometer and measuring at each said value of intensity of the said reflected or transmitted light, summed up over the said spectral interval, for each said area.

Besides, all the said areas are irradiated simultaneously.

Besides, several different substances capable to selectively bind diverse material components are placed in the said areas.

Besides, binding of diverse material components to the said different substances is detected.

Let us explain the second variant of the method and demonstrate that it is its distinctive features that ensure the required technical result.

In this variant of the method, independence of obtained results on uncontrollable variations of intensity of the light being analyzed is provided by placing a scanned Fabry-Perot interferometer along with the sensor layer on pathway of the light from the source to the detector. The base of the said interferometer is modulated. The distribution of the intensity of the said reflected or transmitted light, summed up over the said spectral interval, as a function of base of the scanned Fabry-Perot interferometer, is registered as the said signal. While this takes place, the said base is chosen sufficiently large so that the period of the transmission spectrum of the scanned Fabry-Perot interferometer is at least twice as small as the width of spectral interval of the wavelengths participating in formation of the registered signal. With regard to a Fabry-Perot interferometer, the term "base" means the length of optical path between mirrors. The mentioned condition implied on base of the scanned Fabry-Perot interferometer means that the spectral characteristic of transmission (reflection) of the interferometer contains at least two maximums. Accordingly, the Fabry-Perot interferometer does not serve for extraction of monochromatic light, i.e. it is not a spectrum analyzer. Unlike the first variant of the method and the method-analogue, this variant does not include registration of the spectrum of the light reflected from the sensor layer or transmitted through the sensor layer.

In this variant of the method, another principle is used instead of the spectrum registration. The scanned Fabry-Perot interferometer and the sensor layer are arranged on the pathway of light participating in formation of the signal to be registered, the said interferometer being placed on the light pathway before the sensor layer or vise versa. Frequency spectrum of transmission (reflection) of the Fabry-Perot interferometer represents a periodic function, whose maximums (minimums) are separated by frequency intervals $$\Delta v = c/2L \qquad (3),$$

where L is interferometer base. Consecutive interaction of light with the sensor layer and the Fabry-Perot interferometer results in superposition of spectral characteristics of these interactions. Therefore, intensity of output light summed up over all used wavelengths is governed by correlation between spectral characteristics of interaction of the light with the Fabry-Perot interferometer and the sensor layer. The latter characteristic, as was discussed above, is due to interference on the sensor layer, its frequency period is described by formula (1), which is similar to formula (3). It follows from the stated above that the correlation signal depends upon the value of the interferometer base. It is the dependence, which is registered in this variant of the method, when the interferometer base is modulated. It should be noted that the dependence of the intensity of the light is registered upon a relative, not the absolute, value of the interferometer base, i.e. upon variation of the base with respect to some initial or mean value. If the spectral position of at least some maximums of the characteristic of interaction of the light with the Fabry- Perot interferometer and the characteristic of interaction of the light with the sensor layer coincide, a maximum of the correlation signal is observed in the registered dependence of the light intensity upon the interferometer base. If the optical thickness of the sensor layer equals the interferometer base, an absolute correlation maximum is observed. The wider the frequency spectrum of the light affecting the sensor layer is and the more frequency periods of interference on the sensor layer and frequency periods of the characteristic of the Fabry-Perot interferometer fit into the spectrum width, the more pronounced the absolute correlation maximum among the other correlation maximums is.

It is important to mention that in the proposed variant of the method the light beams that interact with the sensor layer and the Fabry-Perot interferometer and contribute into the recorded signal should be sufficiently collimated. First, for various beams and all wavelengths, which contribute into the recorded signal, the optical path of the light inside the sensor layer should differ by not more than approximately a fourth of wavelength. Second, the beams' directions should be within one angular transmission maximum of the Fabry-Perot interferometer. In multi-channel modifications of the method, such collimation should be provided separately in each channel or each area of the sensor layer, which is analyzed independently.

The correlation signal that governs intensity of the output light depends not only upon base of the Fabry-Perot interferometer, but also upon optical thickness of the sensor layer. The plotted dependence of the correlation signal on the interferometer base shifts along the axis of the interferometer base values, with a change of the said thickness. In particular, the values of the base, at which maximums of the correlation signal are observed, change. In this variant of the method, judgment about the binding, which is the subject of investigation (the object of detection), is made from analysis of changes of the intensity distribution of the output light over the interferometer base, which are due to the said binding.

Thus, in this variant of the method the information signal is formed based on registration of position of the correlation dependence (as a rule, position of correlation maximums) with respect to the axis of values of the interferometer base. Hence, in contrast to the analogues [DE 42 00 088 C2, Int. Cl. G01N 21/45, 1997 and U.S. Pat. No. 5,999,262, Int. Cl. G01B 9/02, U.S. Cl. 356/357, 1999], variations of intensity of both analyzed light as a whole and parts of the recorded spectrum do not affect the information signal, which provides the said technical result.

The required technical result is achieved also in respect of simplification of the method, diminishing the number of necessary operations, decreasing of labor input and cost. Similarly to the described earlier variant of the proposed method and unlike the analogues [DE 42 00 088 C2, Int. Cl. G01N 21/45, 1997 and U.S. Pat. No. 5,999,262, Int. Cl. G01B 9/02, U.S. Cl. 356/357, 1999], this variant does not require analytical fitting of regions of spectral dependences and obtaining information about absolute value of the sensor layer thickness, because it uses relative measurements. It is a much simpler operation, which concurrently provides much higher precision.

To realize this variant of the proposed method different types of scanned Fabry-Perot interferometers known from the state of the art can be used. In particular, the preferable types are: a) Fabry-Perot interferometers being scanned due to a change of refraction index of a medium between mirrors, made most often on the basis of liquid crystals; b) Fabry-Perot interferometers being scanned due to a change of inter-mirror distance by piezoelectric drivers; c) scanned Fabry-Perot interferometers, in which the inter-mirror distance is changed by electrostatic forces. The scanning frequency of Fabry-Perot interferometers known from the state of the art can be chosen rather high (for some types up to tens kHz) so that the scanning time and, if necessary, signal acquisition interval is much smaller than the characteristic time of the binding to be detected (as a rule, binding time is of order of minutes). This provides possibility to register binding of components in real-time.

It should be noted that this variant of the proposed method can be realized using polychromatic light as well as monochromatic light of a wavelength being tuned within a chosen spectral interval. For example, one can register a correlation signal that is averaged (summed up) over several scanning periods over wavelength, particularly, when the time of scanning over wavelength is significantly less than the time of scanning over the interferometer base. However, the discussed variant of the method is realized in the simplest way and the required technical result is achieved to the maximal degree, when polychromatic light with continuous spectrum is used as the light that irradiated the sensor layer, the coherence length of the said polychromatic light and the said reflected or transmitted light being less than double base of the scanned Fabry-Perot interferometer . Using polychromatic light with continuous spectrum provides the simplest extraction of the information signal and diminishes the number of necessary operations. The mentioned condition for coherence length means that there are at least two periods of the characteristic of the Fabry-Perot interferometer within the width of spectrum of irradiating light and of the reflected or transmitted light being registered (see above). To obtain a pronounced correlation signal it is important also that there are not less than two periods of the spectral distribution due to interference on the sensor layer within the same spectral width. For this, polychromatic light with coherence length that is less than the double thickness of the sensor layer is used.

In the discussed here second variant of the method, information about binding being detected and correspondent change of optical thickness of the sensor layer can be obtained from arbitrary changes of distribution of intensity of the output light over values of the scanned Fabry-Perot interferometer base. In particular, the changes can be registered on a slope or in a minimum of this distribution. However, one can provide independence on variations of the light intensity in the simplest way and achieve the required technical result to the maximal extent if at least one intensity maximum due to correlation between spectral characteristics of interaction of light with the sensor layer and the scanned Fabry-Perot interferometer is registered in the said distribution; and information about binding being detected is obtained from a change of position of the said at least one maximum with respect to values of base of the scanned Fabry-Perot interferometer. This can be an absolute correlation maximum at coincidence of the base and optical thickness of the sensor layer as well as any side maximum. One can also observe a number of correlation maximums in the said distribution and register a displacement of the said distribution as a whole along values of the interferometer base.

Depending on a particular application of the method, the scanned Fabry-Perot interferometer is placed on the pathway of light, in which the said signal is registered, before its incidence onto the sensor layer or on the pathway of the said reflected or transmitted light, in which the said signal is registered, after its reflection from the sensor layer or transmission through the sensor layer, respectively. In particular, the former method is preferable when it is necessary to irradiate the sensor layer by a wide beam. Then it is reasonable to send a narrow light beam to the Fabry-Perot interferometer, which makes the requirements of parallelism of the interferometer mirrors and their out-of-flat displacement less strict, and then widen the beam to irradiate the sensor layer. This approach is especially preferable in multi-channel realizations of the method.

To achieve the required technical result, depending also on particular applications of the method, used optical schemes, characteristics of components and operational modes of these schemes, it is reasonable to use the scanned Fabry-Perot interferometer either in the reflection mode or transmission mode.

Additional features of the second variant of the method coincide with the additional features of the first variant of the method, which were discussed above and have the same meaning for achievement of the technical result. For this reason, these are not discussed here.

In multi-channel modifications of the second variant of the method, binding of at least one material component is detected in several spatially separated areas of the irradiated region on the sensor layer, the said distribution is registered for each said area and the said spectrum is used as the said signal for each said area. The method is similar to a method with the only difference, namely, the distribution of intensity of the said reflected or transmitted light, summed up over the used spectral interval, as a function of base of the scanned Fabry-Perot interferometer is registered for each said area instead of the spectrum. With this consideration, the above discussion is valid and is not further discussed here.

The preferable realization of the multi-channel method consists in registration of the said distribution for each said area by using sequentially in time different values of base of the scanned Fabry-Perot interferometer and measuring at each said value the intensity of the said reflected or transmitted light, summed up over the said spectral interval, for each said area. This allows recording of the said distribution point-by-point in parallel for all said areas of the sensor layer, each point corresponding a single value of the interferometer base. In this case, it is sufficiently to use only one scanned Fabry-Perot interferometer to study binding of components in a large number of areas of the sensor layer. This simplifies the method, makes it more cost-efficient and provides the required technical result. The simplest multi-channel modification is realized when all the areas are simultaneously irradiated by light. For example, the interferometer is located before the sensor layer on the pathway of the parallel light beam; the beam is widened after the interferometer, e.g. by a telescopic scheme; the resulting wide parallel beam is used for irradiating of all said areas. It is the simplest realization of the proposed variant of the method, which provides maximal accuracy and reliability of measurement results, and, consequently, the required technical result.

Additional features of the second variant of the method coincide with features of the first variant of the method discussed above and are not considered here.

Thus, we showed that the required technical result is actually realized due to essential differences of the proposed variants of the method.

The third variant of the method of optical detection of binding of at least one material component to a substance located on a surface of or inside a sensor layer due to a biological, chemical or physical interaction is proposed, which comprises:
  irradiation of the sensor layer by light of various wavelengths, for which the sensor layer is transparent, at least, partially;
  registration in the reflected or transmitted light of a signal, which depends upon optical thickness of the said sensor layer and is due to the fact that interference on the said sensor layer modulates the said reflection or transmission spectrum of the said sensor layer, respectively;
  judging about the binding being detected from a change of the said signal,
    which is similar to the method-analogue.

The proposed variant of the method is characterized in that:
  on the pathway of the light from the source to the detector a scanned interferometer is placed along with the sensor layer;
  the path difference of beams of the said scanned interferometer is chosen sufficiently large so that the period of the transmission spectrum of the said scanned interferometer is at least twice as small as the width of spectral range of wavelengths participating in formation of the recorded signal;
  the path difference of beams of the said scanned interferometer is modulated;
  distribution of intensity of the said reflected or transmitted light, summed up over the said spectral interval, as a function of the path difference of beams of the said scanned interferometer is registered as the said signal.

This variant of the method is similar to the second variant of the method due to employment of other interferometers, e.g. Mickelson, Mach-Zahnder interferometers or other interferometers, including fiber-optical ones, without any change of technical entity. The said additional features of the second variant of the method are applicable for the third variant of the method. However, in this case, scanning of the interferometer is done by changing the path difference of interfering beams (or arms) of the interferometers.

The experiments showed feasibility of the proposed variants of the method.

To achieve the said technical result and to realize the first variant of the proposed method an apparatus (first variant) is proposed for optical detection of binding of at least one material component to a substance located on a surface of or inside a sensor layer due to a biological, chemical or physical interaction, which comprises:
  a sensor layer;
  a source of light, which irradiates the sensor layer, of wavelengths that include at least operating wavelengths, for which the sensor layer is transparent, at least, partially;
  a detector, which is placed on the pathway of the light reflected from the sensor layer or transmitted through the sensor layer, for measuring the light intensity of operational wavelengths in the spectrum of the received light;
  a block of result generation, for example, a computer, to generate information about the binding being detected on the basis of changes of the said spectrum, whose input is connected to the output of the detector,
    which coincide with essential features of the apparatus-analogue.

The proposed apparatus is characterized in that:
the thickness of the said sensor layer is more than 10 µm and, at the same time, exceeds the maximal operating wavelength by at least one order of magnitude;
either the source radiates collimated light or a means of collimating the light is introduced on the pathway of the light from the source before the sensor layer so that the sensor layer is irradiated by collimated light.

Besides, the source is monochromatic with tunable wavelength, and the detector is a photodetector.

Besides, the source is a tunable laser, e.g. tunable semiconductor laser.

Besides, the source is made of a source of polychromatic light combined with a tunable monochromator or tunable spectral filter.

Besides, the source is a set of monochromatic sources of different wavelengths, made with capability to switch them successively in time.

Besides, the source is a source of polychromatic light.

Besides, polychromatic light of the source has continuous spectrum with coherence length that is less than double thickness of the sensor layer.

Besides, the detector is a matrix spectrometer.

Besides, the detector is made of a photodetector combined with a tunable monochromator or tunable spectral filter.

Besides, the source is made based on a lamp.

Besides, the source is made based on a light-emitting diode or superluminescent laser diode.

Besides, the sensor layer is located on a substrate.

Besides, light from the source irradiates the sensor layer from the substrate's side, the substrate being transparent, at least partially, for the said light.

Besides, the sensor layer is formed by a plate with surfaces not-adjacent to any substrate.

Besides, one of the boundary surfaces of the sensor layer, toward which the light from the source is directed, contacts the liquid under test, which contains or presumably contains a biological or chemical component, whose binding is the object of detection; a substance for amplification or attenuation of reflection is present on another boundary surface, both boundary surfaces having close reflection coefficients.

Besides, both boundary surfaces of the sensor layer, toward which light from the source is directed, contact liquids; at least one of these liquids being the liquid under test, which contains or presumably contains the biological or chemical component, whose binding is the object of detection; the refractive index of the second liquid is close to the refractive index of the liquid under test.

Besides, both said boundary surfaces contact the liquid under test, a substance capable to bind the said biological or chemical component being present on both said boundary surfaces.

Besides, the sensor layer is formed by a layer of the liquid under test, which contains or presumably contains the biological or chemical component, whose binding is the object of detection; the boundary surfaces of the said layer, which are irradiated by light from the source, are formed with using of hard optical materials.

Besides, variation of optical thickness of the sensor layer within the irradiation spot of light that is directed from the source toward the sensor layer and further to the detector, does not exceed a fourth of wavelength for the least operating wavelength.

Besides, the sensor layer consists of several spatially separated areas or comprises several spatially separated areas, which are irradiated by light from the source, no area overlapping light incident to another area; the detector is made capable to measure intensity of received light for each said area; the block of result generation is made capable to analyze changes of the said spectrum for each said area and generate information about binding being detected based on such changes.

Besides, the sensor layer in each of the said areas is formed by a plate, which shapes the bottom of a reaction cell and is not adjacent to any substrate; the reaction cells produce an array, e.g. a microtiter plate.

Besides, the sensor layer forms the bottom of a reaction cell in each said area and is located on a substrate that is transparent for operating wavelengths; the reaction cells produce an array, e.g. a microtiter plate.

Besides, variation of optical thickness of the sensor layer within each said area does not exceed a fourth of wavelength for the least operating wavelength.

Besides, the source is polychromatic and the detector is a set of matrix spectrometers for registration of the spectrum of received light for each said area.

Besides, the said matrix spectrometers are furnished by optical fibers for input of light from the said areas.

Besides, an optical system to project light from the said areas to the detector is located on the pathway of light before the detector; the detector comprises a set of photodetecting zones, each zone having independent output connected with the block of result generation.

Besides, the said optical system is made on the basis of a parabolic mirror.

Besides, the proposed apparatus differs in that:
the source is monochromatic with tunable wavelength;
in each said area the sensor layer is formed by a plate with surfaces not adjacent to any substrate;
a control link is introduced between the block of result generation and the source to switch the latter to another wavelength of irradiated light after measurement by the detector of the intensity of the received light for each said area at one wavelength;
the block of result generation is made capable to generate a spectral distribution of intensity of light measured by a detector over wavelength for each said area.

Besides, the proposed apparatus differs in that:
the source is monochromatic with tunable wavelength;
in each said area the sensor layer is formed by a layer of the liquid under test, which contains or presumably contains the biological or chemical component, whose binding is the object of detection; the boundary surfaces of the said layer, which are irradiated by light from the source, are formed with using of hard optical materials;
a control link is introduced between the block of result generation and the source to switch the latter to another wavelength of irradiated light after measurement by the detector of the intensity of the received light for each said area at one wavelength;
the block of result generation is made capable to generate a spectral distribution of intensity of light measured by the detector over wavelength for each said area.

Besides, the proposed apparatus is characterized in that:
the source is polychromatic;
there is a tunable monochromator or tunable spectral filter placed on the light pathway before the detector;
a control link is introduced between the block of result generation and the said tunable monochromator or tunable spectral filter to switch the latter to another wavelength after measurement by the detector of the intensity of the received light for each said area at one wavelength;
the block of result generation is made capable to generate a spectral distribution of intensity of light measured by the detector over wavelength for each said area.

Besides, different substances capable to selectively bind different material components from a gaseous or liquid medium are located in the said areas.

As a realization of the second variant of the proposed method the second variant of the apparatus is proposed, which is intended for optical detection of binding of at least one material component to a substance located on a surface of or inside the sensor layer due to a biological, chemical or physical interaction. The apparatus comprises:
- a sensor layer;
- a source of light, which irradiates the sensor layer, of wavelengths that include at least operating wavelengths, for which the sensor layer is transparent, at least, partially;
- a detector, which is placed on the pathway of the light reflected from the sensor layer or transmitted through the sensor layer, for measuring intensity of light of operating wavelengths;
- a block of result generation, for example, a computer, to generate information about the binding being detected, whose input is connected to the output of the detector, which coincide with essential features of the apparatus-analogue.

The proposed apparatus is characterized in that:
- on the pathway of the light from the source to the detector a scanned Fabry-Perot interferometer with modulated base (i.e. length of optical path between the mirrors) is placed along with the sensor layer;
- the base of the scanned Fabry-Perot interferometer is sufficiently large so that the related period of the transmission spectrum of the said scanned Fabry-Perot interferometer is at least twice as small as the width of spectral range, corresponding to operating wavelengths;
- block of signal generation is made capable to register distribution of the light intensity measured by the detector, summed up over the operating wavelengths, as a function of base of the scanned Fabry-Perot interferometer and generate information about the binding being detected on the basis of a change of the said distribution.

Besides, light from the source, which irradiates the sensor layer and the scanned Fabry-Perot interferometer, is collimated, i.e. a source of collimated light is used as the light source and/or means for collimation of the light are introduced before the sensor layer and/or the scanned Fabry-Perot interferometer;

Besides, the source is a source of polychromatic light with continuous spectrum and coherence length that is less than the double base of the scanned Fabry-Perot interferometer.

Besides, the coherence length of the said polychromatic light is less than the double thickness of the sensor layer.

Besides, the source is made on the basis of a lamp.

Besides, the source is made on the basis of a light-emitting diode or superluminescent laser diode.

Besides, the scanned Fabry-Perot interferometer is introduced in the optical scheme as a reflecting element.

Besides, the scanned Fabry-Perot interferometer is introduced in the optical scheme as a transmitting element.

Besides, the scanned Fabry-Perot interferometer is located on the pathway of light from the source to the sensor layer.

Besides, at least part of the path from the source to the scanned Fabry-Perot interferometer and/or from the scanned Fabry-Perot interferometer to the sensor layer the light travels inside an optical fiber.

Besides, the scanned Fabry-Perot interferometer is located on the pathway of light from the sensor layer to the detector.

Besides, the sensor layer is located on a substrate.

Besides, light from the source irradiates the sensor layer from the substrate's side, the substrate being transparent, at least, partially, for the light:

Besides, the sensor layer is formed by a plate with surfaces not adjacent to any substrate.

Besides, one of the boundary surfaces of the sensor layer, towards which the light from the source is directed, contacts the liquid under test, which contains or presumably contains the biological or chemical component, whose binding is the object of detection; a substance for amplification or attenuation of reflection is present on another boundary surface, both boundary surfaces having close reflection coefficients.

Besides, both boundary surfaces of the sensor layer, toward which light from the source is directed, contact liquids, at least one of these liquids being the liquid under test, which contains or presumably contains the biological or chemical component, whose binding is the object of detection.

Besides, both said boundary surfaces contact the liquid under test, a substance capable to bind the said biological or chemical component being present on both said boundary surfaces.

Besides, the sensor layer is formed by a layer of the liquid under test, which contains or presumably contains the biological or chemical component, whose binding is the object of detection; the boundary surfaces of the said layer, which are irradiated by light from the source, are formed with using of hard optical materials.

Besides, variation of optical thickness of the sensor layer within the irradiation spot by light that is directed from the source toward the sensor layer and further to the detector, does not exceed a fourth of wavelength for the least operating wavelength.

Besides, the sensor layer consists of several spatially separated areas or comprises several spatially separated areas, which are irradiated by light from the source, no area overlapping light incident to another area; the detector is made capable to measure intensity of the received light for each said area; the block of result generation is made capable to analyze changes of the said distribution for each said area and generate information about the binding being detected based on such changes.

Besides, the sensor layer in each said area forms the bottom of a reaction cell, and the reaction cells produce an array, e.g. in the form of a microtiter plate.

Besides, variation of optical thickness of the sensor layer within each said area does not exceed a fourth of wavelength for the least operating wavelength.

Besides, an optical system to project light from the said areas to the detector is arranged on the pathway of light before the detector; the detector comprises a set of photodetection zones, each zone having independent output connected with the block of result generation.

Besides, the said optical system is made on the basis of a parabolic mirror.

Besides, the proposed apparatus is characterized in that:
- the source is a source of polychromatic light with continuous spectrum and coherence length that is less than the double base of the scanned Fabry-Perot;
- a control link is introduced between the block of result generation and the scanned Fabry-Perot interferometer to switch the latter to another value of the base after measurement by the detector of the intensity of the received light for each said area at one value of the base;
- the block of signal generation is made capable to obtain distribution of intensity of the light measured by the detector, summed up over the operating wavelengths, at various values of the scanned Fabry-Perot base for each said area.

Besides, different substances capable to selectively bind different material components from a gaseous or liquid medium are arranged in the said areas.

Besides, an optical system for projection of image of the sensor layer onto the detector is arranged on the pathway of light before the detector; the detector comprises a set of photodetector zones; each zone has an independent output connected with the block of signal generation.

As a realization of the third variant of the proposed method the third variant of the apparatus is proposed, which is intended for optical detection of binding of at least one material component to a substance located on a surface of or inside the sensor layer due to a biological, chemical or physical interaction. The apparatus comprises:

a sensor layer;
a source of light, which irradiates the sensor layer, of wavelengths that include at least operating wavelengths, for which the sensor layer is transparent, at least, partially;
a detector, which is placed on the pathway of the light reflected from the sensor layer or transmitted through the sensor layer, for measuring intensity of light of operating wavelengths;
a block of result generation, for example, a computer, to generate information about the binding being detected, whose input is connected to the output of the detector, which coincide with essential features of the apparatus-analogue.

The proposed apparatus is characterized in that:
on the pathway of the light from the source to the detector a scanned interferometer with modulated path difference of beams is placed along with the sensor layer;
the path difference of beams of the said scanned interferometer is sufficiently large so that the related period of the transmission spectrum of the said scanned interferometer is at least twice as small as the width of spectral range, corresponding to operating wavelengths;
block of signal generation is made capable to register distribution of intensity of the light measured by the detector, summed up over the operating wavelengths, as a function of path difference of beams of the scanned interferometer and generate information about the binding being detected on the basis of a change of the said distribution.

Besides, additional features of the second variant of the apparatus extend to the third variant of the apparatus. However, in this case, scanning of the interferometer is done by changing the path difference of interfering beams (or arms) of the interferometer.

Figure 1:
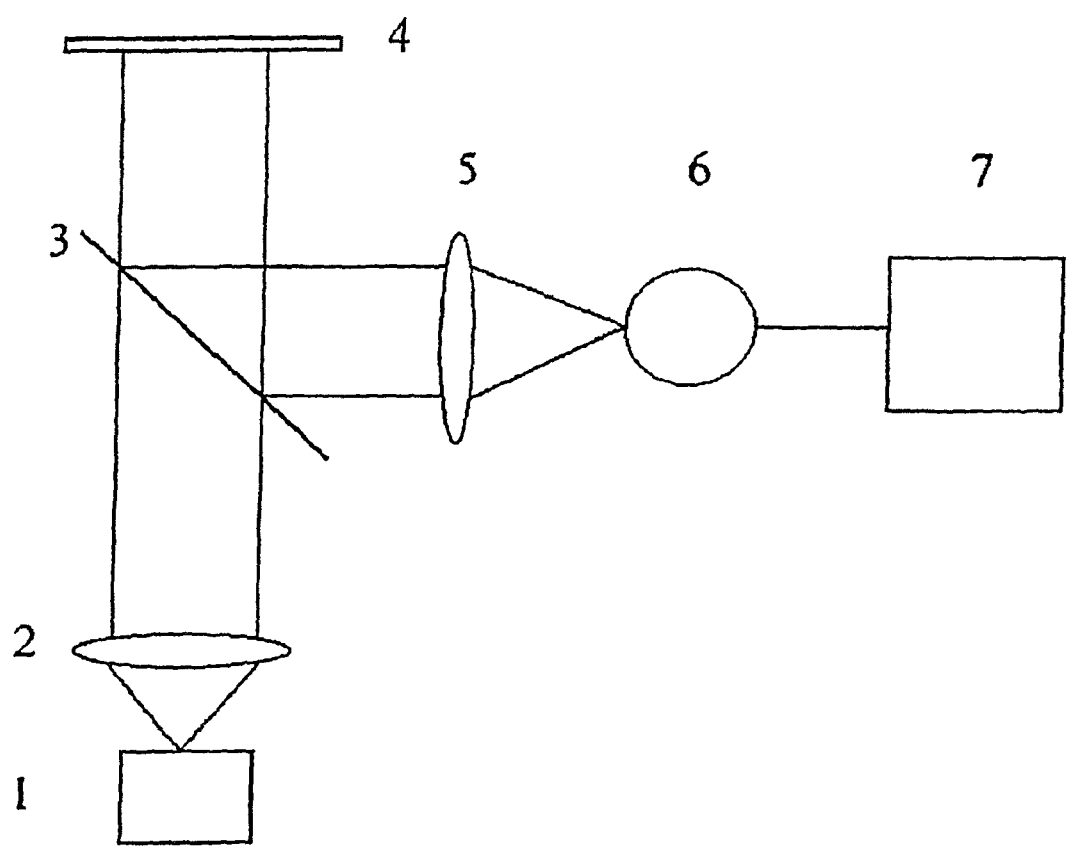
FIG. 1. A scheme of first variant of the proposed apparatus.
Figure 2:
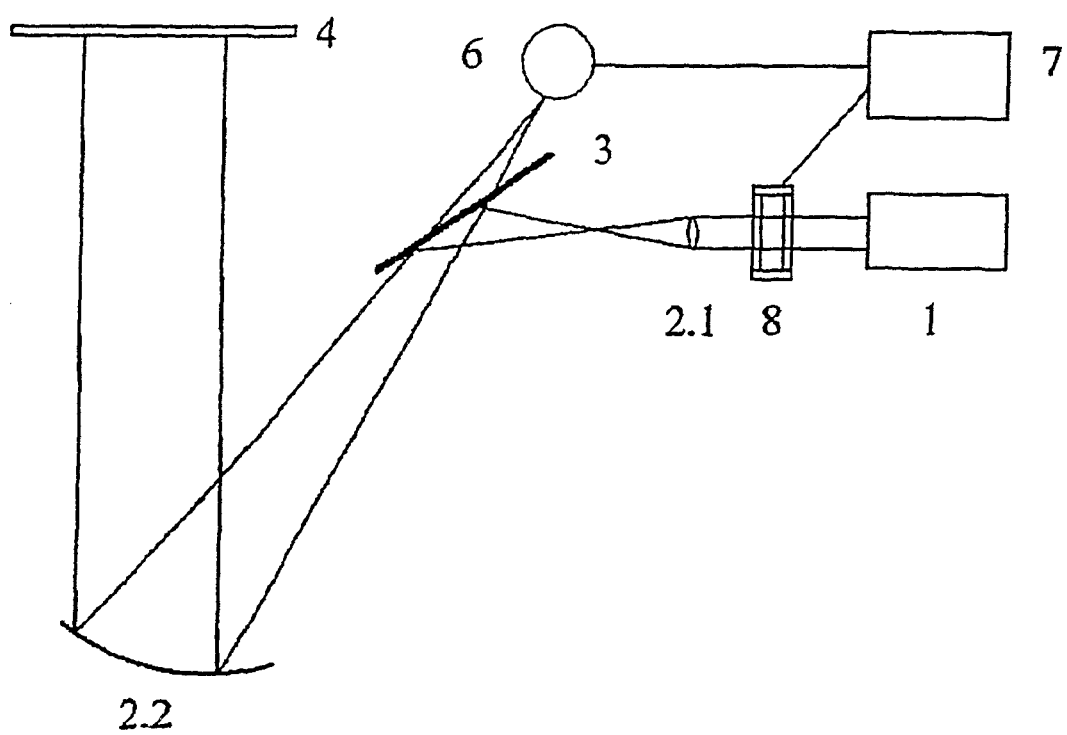
FIG. 2. A scheme of second variant of the proposed apparatus.

The following notations are used in FIG. 1-2: 1—source; 2—means for collimation of light; 2.1 and 2.2 are its components; 3—light-splitting element; 4—sensor layer; 5—optical system for projection of light onto detector; 6—detector; 7—block of signal generation; 8—scanned Fabry-Perot interferometer.

MODES FOR CARRYING OUT THE INVENTION

First variant of the proposed apparatus is schematically shown in FIG. 1. A substance (or several substances) capable to bind material (biological, chemical or other) components due to a biological, chemical or physical interaction is located on a surface of or inside a sensor layer 4. The substance contacts a medium (not shown in FIG. 1) that contains or presumably contains the said components. Biospecific binding (e.g. antigen-antibody, biotin-avidin), formation of chemical associations, adsorption or absorption, etc. can be named among examples of such interactions. For operation of the apparatus it is imperative not the type of interaction, but the fact that any such binding goes with superinduction of a new substance to the surface of or into the sensor layer and causes an increase (a decrease in variants according to certain embodiments, when the sensor layer is formed by the medium under test) of optical thickness of the sensor layer, which is registered by the apparatus. The apparatus can register also reverse reactions of detachment of components from the substance of the sensor layer, because they go with a decrease (an increase in certain embodiments) of optical thickness of the sensor layer.

The sensor layer 4 is irradiated by light from a source 1, which contains simultaneously or separately different operating wavelengths. The operating wavelengths are those of light from the source 1, whose intensity is measured by a detector 6. In general case, there can be present also wavelengths in the spectrum of the source 1 (e.g. incandescent lamp), which are beyond the range of sensitivity of the detector 6 (e.g. produced on the basis of semiconductor photodiodes). The sensor layer 4 is transparent for operating wavelengths to the degree, which provides a possibility to observe interference of secondary light waves that arise on boundary surfaces of the sensor layer 4.

The detector 6 is located on the pathway of light reflected from the sensor layer 4 (this variant of the apparatus is shown in FIG. 1) or transmitted through the sensor layer 4 (this variant is not shown). The difference between the apparatus variants, which use measurements in the reflected and transmitted light, is insignificant, and both variants provide the same technical result. A light-splitting element 3 in the scheme shown in FIG. 1 is one of the said insignificant differences. One can employ, for example, a light-splitting plate (shown in FIG. 1) or a light-splitting cube as the element 3. It is reasonable to use the element 3 for splitting beams of light, which is incident to the sensor layer and reflected from it, in the schemes of the apparatus employed for measurements in the reflected light and the angle of the light incidence onto the sensor layer is close to the normal. In measurements in the transmitted and reflected light at large angles of incidence with respect to the normal to the sensor layer the element 3 is not necessary.

The optical system 5 for projection of light from the sensor layer to the detector is not a necessary element in the apparatus. It is reasonable to employ the system 5 when, for example, there is a substantial difference in size of the irradiated region of the sensor layer 4 and photodetecting zone of the photodetector 6, to prevent significant losses of light and to increase signal-to-noise ratio. The system 5 is used also in a number of multi-channel modifications of the apparatus (see below). Lens or mirror objectives (e.g. with using of a parabolic mirror), telescopic systems, etc. can serve as the system 5.

Operation of the first variant of the apparatus is based on the fact that the detector 6 registers spectrum of the received light by measuring intensity of the light simultaneously or separately at different operating wavelengths. An interference pattern, which is periodic over light frequency with the period described by the relationship (1), is observed in the registered spectrum. A block of signal generation 7 analyzes changes of the said interference pattern, which is due to a change of optical thickness of the sensor layer 4 during binding being detected, and generates information about the binding being detected.

As was mentioned above during analysis of the method, the light beam should be sufficiently collimated to observe the said interference pattern. If the source 1 itself does not provide sufficient collimation of the output light beam (e.g. if the source is a lamp, light-emitting diode or a semiconductor laser), a means 2 for collimating light, which decreases beam divergence, is introduced on the pathway of the light from the source 1 before the sensor layer 4. A collimating objective (lens or mirror), aperture, combination of an objective with an aperture, etc. can serve as examples of the means 2. The means 2 is not employed, if the source 1 is a source of collimated light, e.g. a laser with low divergent output beam.

Contrasting to the apparatus-analogue, in the proposed apparatus large thickness of the sensor layer 4 leads to presence of several interference periods in the recorded spectrum. Therefore, it is not necessary to measure intensity precisely and determine on that basis an absolute thickness of the sensor layer. Instead, a spectral shift of individual interference maximums or minimums, or of whole "comb" of maximums or minimums is analyzed, which serves as a source of information about relative changes of optical thickness of the sensor layer 4 and, consequently, about the binding being detected.

Since the spectral position of interference maximums and minimums does not depend upon variations of intensity of the whole spectrum or its parts, the proposed variant of the apparatus provides the required technical result. The more detailed discussion is provided above while analysis of the first variant of the proposed method.

To achieve the required technical result in part of increasing accuracy of measurements with simultaneous decrease of requirements to the detector 6, it is reasonable to implement the scheme of the apparatus, in which the source 1 is monochromatic with tunable wavelength and the detector 6 is a photodetector. Preferable realizations are those, in which the source 1 is a tunable laser, e.g. a tunable semiconductor laser; or the source 1 is made of a source of polychromatic light in combination with a tunable monochromator or tunable spectral filter; or the source 1 is a set of monochromatic light sources of different wavelengths, which is made capable to switch the wavelengths successively in time. Such variants of the apparatus are especially preferable for purposes of multichannel registration.

It should be emphasized that a qualitative difference of the first variant of the proposed apparatus and related method from the analogue [DE 42 00 088 C2, Int. Cl. G01N 21/45, 1997] is in capability of using tunable lasers as the light source. The tuning range of such lasers is commonly quite narrow, so in the analogue it could only be a small part of width of the spectrum necessary to find optical thickness of the sensor layer and detect binding of components. In the proposed method and apparatus, using of large thickness of the sensor layer provides presence of several interference periods within tuning range of the laser, which is sufficient for high precision detection of binding of components. Thus, in contrast to the analogue, in the proposed method and apparatus it is possible to use tunable lasers and other monochromatic sources tunable in narrow spectral ranges, and also polychromatic sources with narrow spectral range, e.g. light-emitting diodes or superluminescent laser diodes (see below).

Extra opportunities are open, if the source 1 is a source of polychromatic light . Requirements to the source are weaker, and the number of operations is smaller, which makes the apparatus simpler and more cost-efficient, especially at registration on one channel or small number of channels. In this case, it is reasonable to use light with continuous spectrum and coherence length that is less than double thickness of the sensor layer 4. Continuity of the spectrum permits one to obtain the spectral position of interference maximums or minimums with maximal precision. The mentioned condition for coherence length means that there are at least two interference maximums or minimums of intensity of the transmitted or reflected light within spectral width of the used polychromatic light.

The apparatus with using of polychromatic light, in which the detector 6 is a matrix spectrometer is especially preferable for simplicity of realization, reproducibility of results and diminishing of the number of necessary operations. As a rule, the matrix spectrometer is made based on a dispersion element, e.g. a diffraction grating, combined with a matrix photodetector such as an array of photodiodes or a CCD-array. Usually, a linear (one-dimensional) array (matrix) oriented along the dispersion direction is used. Light is supplied into such spectrometer through an aperture (slot) or an optical fiber. The matrix spectrometer permits one to register simultaneously (taking into account acquisition time) the whole required spectrum and avoid scanning over the spectrum. However, depending on particular applications, the detector 6, which is made based on a photodetector combined with a tunable monochromator or tunable spectral filter, can be used in combination with a source of polychromatic light.

It is reasonable to make the source of polychromatic light based on a lamp or a light-emitting diode. In the first case, there is a widest spectrum of the source, which provides versatility for registration of the spectrum in various ranges of wavelengths, and choice of a desirable and rather large number of interference periods within the width of the recorded spectrum. In the latter case, the largest spectral density of power of the used polychromatic light is provided, which is profitable for increasing of the signal-to-noise ratio. It should be noted that due to large thickness of the sensor layer, several periods of interference can be registered within spectrum of a light-emitting diode, which is an important difference from the analogue.

Features of the apparatus were considered above in connection with an analysis relevant to the first variant of the method, so the corresponding discussion is not repeated here. It should be noted only that in the apparatus that realizes the method for investigation of binding of a component (components) from the side of both boundary surfaces of the sensor layer, there is a substance capable to bind respective component (components) on both said boundary surfaces. For example, it can be an antigen for binding a corresponding antibody, streptavidin for binding biotinylated proteins, nucleotide chains for binding complementary nucleotide sequences and other substances for specific binding. Non-specific binding can be also used.

An important feature of the proposed apparatus is that a variation of optical thickness of the sensor layer 4 within the irradiation spot by light directed from the source 1 to the sensor layer 4 and further to the detector 6 does not exceed a fourth of wavelength for the least operating wavelength. The said restriction on the thickness variation refers to the irradiation spot of the light, which contribute to generation of the information signal registered by the detector 6. Optical thickness of the sensor layer in every point of its surface is described by expression (2) that takes into account a distribution of refraction index over the layer thickness, the refraction index and, consequently, optical thickness, being dependent on light wavelength. At large variations of optical thickness over the irradiated region maximums and minimums of interference patterns in spectra of different areas would overlap, there would occur a decrease of contrast, blurring or, maybe, even disappearance of the well-defined interference pattern in the resulting spectrum averaged over the irradiated region. However, if these variations do not exceed a fourth of wavelength for the least wavelength of the registered spectrum, then a distinct interference pattern is observed over whole registered spectrum, which permits one to achieve the required technical result.

An apparatus for multi-channel registration of binding components is realized as follows: the sensor layer 4 consists of several spatially separated areas or comprises several spatially separated areas, which are irradiated by light from the source 1; no area overlaps light incident to another area; the detector 6 is made capable to measure intensity of the received light for each said area; the block of signal generation 7 is made capable to analyze changes of the said spectrum for each said area and generate information about the binding being detected on the basis of these changes. Principles of multi-channel registration, fields of application and provision of the required technical result were discussed above while analysis of the method. The registration channels correspond to spatially separated areas of the irradiated region or groups of the said areas of the sensor layer, and the information signal (in the first variant of the method and apparatus—the spectrum) is recorded for each area separately and independently of other areas. The block of signal generation generates information about binding being detected for either each said area or a group of the said areas, e.g. by averaging of information signals over the group of areas.

In some cases, the said areas can be chosen or fowled on a surface of a continuous sensor layer (a film, plate or liquid layer), for example, by deposition of different binding (recognition) reagents onto various regions of the surface. If the binding being detected takes place on both boundary surfaces of or inside the sensor layer, then regions of the said two surfaces or volume, which are irradiated by the same beams from the source, are considered as a single area. In other cases, the sensor layer can be non-continuous and represents a set of spatially separated areas, e.g. bottom plates of an arbitrary set of reaction cells.

In particular, in one preferable realization the sensor layer in each said area is formed by a plate, which shapes the bottom of a reaction cell and is not adjacent to any substrate, and the reaction cells produce an array, e.g. a microtiter plate. In another preferable realization of the apparatus, the sensor layer in each said area forms the bottom of a reaction cell and is located on a substrate that is transparent for operating wavelengths, and the reaction cells produce an array, e.g. a microtiter plate. In both cases, there can be either a single area of the sensor layer, a signal from which is registered separately and independently from other areas, or several said areas within one cell. Fabrication of the base element of the apparatus as a microtiter plate provides compatibility with standard formats of biological and biochemical analyses, decreases cost of the apparatus and the number of necessary operations, extends the field of application, providing the required technical result.

For the multi-channel apparatus, it is important that variation of optical thickness of the sensor layer within each said area does not exceed a fourth of wavelength for the least operating wavelength, i.e. the discussed above restriction on variation of thickness within the irradiation spot should be extended to each area of the sensor layer, the signal from which is registered separately and independently from other areas.

At a relatively small number of channels the required technical result is provided maximally if the source is polychromatic, the detector is a set of matrix spectrometers for registration of spectrum of the received light for each said area, one area being correspondent to one registration channel (one reaction cell). This allows registration of the whole spectrum in each channel, avoiding thus scanning over spectrum. This also decreases the number of necessary operations and time consumption, increases accuracy, reliability of results and time resolution, which is important for real-time registration. There are extra opportunities if the said matrix spectrometers are furnished by optical fibers to input light from the said areas so that the light from the said areas is supplied to the spectrometers. This permits one to miniaturize the said areas to the size of about the fibers' diameter, diminish weight and dimensions of the whole apparatus, makes possible remote investigations, when the detector is located at a significant distance.

In other cases, in particular, at a large number of channels, an optical scheme 5 for projection of light from the said areas to the detector 6 is placed on the pathway of the light before the detector 6; the detector 6 comprises a set of photodetecting zones, each zone having independent output connected with the block of result generation 7. The photodetector 6 can be made as a set of photodetectors, a two-dimensional photodetector array, a CCD-array, or a camcorder. In these cases, an area of the sensor layer, a signal from which is registered separately and independently from other areas, is an area of the sensor layer, the light from which is projected onto the same photodetecting zone. One or several said areas (in preferable variants, a large number of the said areas and large number of photodetecting zones) correspond to one reaction cell (one registration channel). It should be emphasized, that the restriction discussed above concerning variation of optical thickness of the sensor layer refers to only one said area, not to the whole reaction cell. Therefore, with increase of the number of the said areas and, accordingly, photodetecting zones per one reaction cell, the requirements to evenness of thickness of the sensor layer within the reaction cell decrease. This significantly reduces cost of the apparatus and contributes to achievement of the required technical result. In addition, accuracy and reliability of results of measurements increase due to averaging of the signals from individual areas over the whole irradiated region of the sensor layer within the reaction cell.

The said optical system 5 serves usually for both deflection and focusing of light beams, because dimensions of photodetecting zones of the detector 6 are typically considerably less than dimensions of areas of the sensor layer under study, for example, in the case, when the sensor layer 4 matches a microtiter plate of typical size. Such optical system 5 may comprise, for example, a lens or mirror objective, telescopic system, etc. The system 5 can generate an image of the sensor layer 4 on the detector 6. However, this is not necessary due to the use of collimated light. In preferable realization of the apparatus, the said system is made on the basis of a parabolic mirror. This allows one to use small photodetector arrays, minimize the optical path from the sensor layer to the detector, and minimize weight and dimensions of the apparatus, simultaneously avoiding aberrations. This increases sensitivity of the apparatus and accuracy of measurements.

To achieve the required technical result in the apparatus in one embodiment, it is reasonable to provide registration of the spectrum modulated by interference on the sensor layer by scanning over the spectrum, i.e. by measuring intensity in the spectrum sequentially at different wavelengths. This considerably simplifies the apparatus due to reduced requirements to the multi-spot detector: it is necessary to measure intensity of the light incident to each spot, not to register its spectrum. There is further potential to simplify and reduce cost of the apparatus in using a thick sensor layer in the form of a plate. In such apparatus:

the source is monochromatic with tunable wavelength;

in each said area the sensor layer is formed by a plate with surfaces not adjacent to any substrate;

a control link is introduced between the block of result generation and the source to switch the latter to another wavelength of irradiated light after measurement by the detector of the intensity of the received light for each said area at one wavelength;

the block of result generation is made capable to generate a spectral distribution of intensity of the light measured by the detector over wavelength for each said area.

In another version the thick sensor layer is formed by the liquid being tested. Advantages of such scheme were discussed above. In such apparatus:

the source is monochromatic with tunable wavelength;

in each said area the sensor layer is formed by a layer of the liquid under test, which contains or presumably contains the biological or chemical component, whose binding is the object of detection; the boundary surfaces of the said layer, which are irradiated by light from the source, are formed with using of hard optical materials;

a control link is introduced between the block of result generation and the source to switch the latter to another wavelength of irradiated light after measurement by the detector of the intensity of the received light for each said area at one wavelength;

the block of result generation is made capable to generate a spectral distribution of intensity of the light measured by the detector over wavelength for each said area.

Another option to scan over the spectrum is changing of wavelength of the radiation received by the detector, not the radiation emitted by the source. In the corresponding apparatus:

the source is polychromatic;

there is a tunable monochromator or tunable spectral filter placed on the light pathway before the detector;

a control link is introduced between the block of result generation and the said tunable monochromator or tunable spectral filter to switch the latter to another wavelength after measurement by the detector of the intensity of the received light for each said area at one wavelength;

the block of result generation is made capable to generate spectral distribution of intensity of the light measured by the detector over wavelengths for each said area.

To make all the mentioned multi-channel modifications of the apparatus applicable to simultaneous registration of binding of different components of gaseous and liquid media as well as analysis of presence of simultaneously several components in gaseous and liquid media, providing the required technical result (see above the analysis of the method), there are different substances, which are capable to selectively bind different material components from a gaseous and liquid medium, arranged in the said areas.

The second variant of the proposed apparatus (one of possible schemes) is schematically shown in FIG. 2. The sensor layer 4 is irradiated by light from the source 1, which contains simultaneously or separately different operating wavelengths. As already discussed for the first variant of the apparatus, a substance that realizes the binding being detected, which causes a change of optical thickness of the sensor layer, is arranged on the surface of or inside the sensor layer 4. The sensor layer is transparent for operating wavelengths to the degree, which provides possibility to observe interference of secondary light waves that arise on boundary surfaces of the sensor layer. As a result of such interference, the transmission and reflection spectra of the sensor layer are a modulated intensity distribution with a period on the light frequency described by relationship (1). Only the scheme that uses light reflected from the sensor layer is shown in FIG. 2. The scheme that uses transmitted light differs insignificantly (in particular, as in the first variant, it does not require the light-splitting element 3) and provides the same technical result.

Spectrum of the light at the output of Fabry-Perot interferometer also represents a modulated distribution of intensity with a period on the light frequency described by relationship (3). The base of the scanned Fabry-Perot interferometer 8 in the proposed apparatus is chosen sufficiently large so that the period of the spectral characteristic of the interferometer 8 is at least twice as small as the width of spectral range, corresponding to operating wavelengths. This means that there are at least two maximums of the spectral characteristic of the interferometer within the width of spectrum of the operating wavelengths.

Operation of the second variant of the apparatus is based on the fact that the interferometer 8 is scanned and its base is modulated. Under modulation of base the period and spectral positions of maximums of the spectral characteristic of the interferometer change according to the relationship (3). Contrasting to the apparatus-analogue and first variant of the apparatus, in this variant, the intensity of the light after interaction with the sensor layer 4 and the scanned Fabry-Perot interferometer 8 is registered instead of the spectrum. The said intensity is measured by the detector 6, e.g. a photodetector or photodetector array. The block of signal generation 7 registers the dependence of this intensity upon base of the interferometer 8. When spectral positions of at least several spectral maximums in the characteristics of the interferometer 8 and the sensor layer 4 coincide, a correlation maximum is observed in the said dependence; when positions of all maximums coincide, there is an absolute correlation maximum. When optical thickness of the sensor layer 4 changes as a result of the binding being detected, the dependence of intensity upon base of the interferometer 8 shifts along the base values, which is especially convenient to observe by a shift of the correlation maximums. Analyzing the said shift, the block of signal generation 7 generates and indicates information about the binding being detected.

As was mentioned during analysis of the method, the light beams, which interact with the sensor layer 4 and Fabry-Perot interferometer 8 and contribute to the recorded signal, should be sufficiently collimated. First, variations of optical path inside the sensor layer 4 for different beams and operating wavelengths should not exceed about a fourth of wavelength. Second, directions of the beams should be within one angle transmission maximum of the Fabry-Perot interferometer 8. Because of this, on the pathway of light from the source a means for light collimation can be introduced, which decreases beam divergence if the light from the source is not sufficiently collimated. A collimating objective (lens or mirror), aperture, combination of an objective with an aperture, etc. can serve as examples of the said means. If there are no objects, which change the divergence of the light beam or its size in cross section, between the Fabry-Perot interferometer and the sensor layer, then the said collimating means can be introduced before only one of the said elements (the sensor layer or interferometer), which the light meets first on its pathway from the source. If there are objects, which change the divergence of the beam or its size in cross section (e.g. if at least part of the path from the Fabry-Perot interferometer to the sensor layer the light travels through an optical fiber), then at least one more means for collimation of light is introduced before the second element of the mentioned ones. As an example, a scheme of the apparatus is shown in FIG. 2, in which the source 1 is a source of collimated light incident onto the interferometer 8 (or a means for collimation of light is embedded into the source 1), so a separate means for collimation of light is not provided before the first element, interferometer 8. A means for collimating light 2 is introduced before the second element, the sensor layer 4. The means 2 also serves for divergence of the light beam, directed from the interferometer 8 to the sensor layer 4. It is desirable to illuminate the Fabry-Perot interferometer 8 by a narrow light beam (this decreases requirements to flatness and parallelism of the interferometer mirrors). On the contrary, a wide beam is desirable for illumination of the sensor layer, which increases the signal-to-noise ratio due to averaging over surface of the sensor layer 4. In multi-channel modifications of the apparatus this allows one to register binding of components in a large number of areas of the sensor layer 4 in parallel and independently. In FIG. 2 the means 2 consists of two elements, a lens 2.1 and parabolic mirror 2.2, the mirror 2.2 simultaneously serves as the optical system 5 for projection of the light from the sensor layer 4 to the detector 6.

Additional features of the apparatus in certain embodiments coincide with features of the method discussed above and are not considered here.

Additional features of the apparatus in certain embodiments coincide with features of the first variant of the apparatus discussed above and are not considered here.

Additional features of the apparatus coincide with features of the method discussed in analyzing the method and are not considered here. However, a preferable realization of the apparatus in one embodiment should be mentioned, in which the light travels inside an optical fiber at least part of its way between the source and the scanned Fabry-Perot interferometer and/or the scanned Fabry-Perot interferometer and the sensor layer. This modification provides the required technical result due to decreasing of weight and dimensions, and increasing of functional versatility of the apparatus. In addition, the modification is important for remote measurements.

Additional features of the apparatus in certain embodiments coincide with features of the first variant of the apparatus discussed above and are not considered here. Additional features of the apparatus in one embodiment are similar to features of the first variant of the apparatus with the only difference, namely, the distribution of intensity of light over values of base of the scanned Fabry-Perot interferometer is considered—instead of the spectrum. Taking into account this notice for multi-channel modifications of the second variant of the apparatus, the discussion above is valid, so it is not discussed here.

In one embodiment, there is a multi-channel apparatus that comprises several spatially separated areas of the sensor layer, where the sensor layer in each said area forms the bottom of a reaction cell, and the reaction cells produce an array, e.g. a microtiter plate. Importance of realization of the base element on the basis of the microtiter plate is analyzed above for the first variant of the apparatus. The difference of the second variant is in that there are no restrictions on thickness of the sensor layer due to the principle of operation of this variant of apparatus. Implementation of the sensor layer on a substrate (with an arbitrary set of other layers or without them) or as a separate plate for each said area is also implied.

Additional features of the apparatus according to certain embodiments coincide with features of the first variant of the apparatus discussed above and are not considered here.

An apparatus according to one embodiment is proposed as a realization of a method discussed above and differs in that:
the source is a source of polychromatic light with continuous spectrum and coherence length that is less than the double base of the scanned Fabry-Perot interferometer;
a control link is introduced between the block of result generation and the scanned Fabry-Perot interferometer to switch the latter to another value of the base after measurement by the detector of the intensity of the received light for each said area at one value of the base;
the block of signal generation is made capable to obtain distribution of intensity of the light measured by the detector, summed up over the operating wavelengths, as a function of values of the Fabry-Perot base for each said area.

As was mentioned in discussing one embodiment of the method, there is a scheme that allows point-by-point registration of the said distribution of intensity over values of the interferometer base simultaneously on all channels, taking one value of the interferometer base after another. In this case, one interferometer serves all channels simultaneously and provides high accuracy of measurements. This simplifies the apparatus and provides the required technical result.

Additional feature of the apparatus in one embodiment coincides with the feature of the first variant of a apparatus discussed above and is not considered here.

Additional feature of the apparatus according to one embodiment permits averaging of thickness difference of biomolecular layers while biochemical analyses. In microbiological and bacteriological analyses, it also allows direct calculation of the quantity of bonded biological agents (bacteria, microorganisms, etc.) with spatial resolution along the sensor layer. In this case, the apparatus is highly stable to temperature or other drifts, because only registration of changes of the sensor layer contrast is important.

The third variant of the apparatus is similar to the second variant of the apparatus. However, it employs other interferometers, e.g. Mickelson, Mach-Zahnder interferometers or other interferometers, including fiber-optical ones, without any change of technical entity. In this case, scanning of the interferometer is done by choice of the path difference of interfering beams (or arms) of the interferometer. The mentioned additional features of the second variant of the apparatus are applicable to the third variant of the apparatus.

Additional features of the method and apparatus according to certain embodiments allow one to provide high accuracy of measurements working with scanned interferometers and high spatial resolution of registration of near-surface reactions, particularly with multi-channel implementation of the apparatus.

Thus, it has been shown that the required technical result is achieved due to the essential differences of the proposed variants of the apparatus.

Experiments demonstrated feasibility of the proposed variants.

INDUSTRIAL APPLICABILITY

The proposed invention is intended for detection and investigation of binding of biological and chemical components of media to a substance of sensor layers on the basis of a biological, chemical or physical interaction by registration of optical signals due to interference on these sensor layers. The invention can be applied for real-time registration of the mentioned processes of binding, opposite processes of detachment, and investigation of kinetics of the processes. By registration of parameters of binding of biological and chemical components to sensing materials the invention permits one to determine the content and measure concentrations of the said components in different media under test, mostly in biological solutions. In particular, the invention is applicable for immunological analyses and allows one to register in real-time the binding of antigens and antibodies, and determine their presence in biological solutions without using of radioactive, ferment, fluorescent and other labels. Besides, the invention permits one to carry out parallel biochemical analyses of a large number of probes with high throughput capacity, and also multi-component analyses. The invention is applicable for production of "biochips", "gene chips", optoelectronic "nose" and "tongue", etc.

The invention claimed is:

1. An apparatus for optical detection of binding of at least one material component to a substance located on a surface of or inside a sensor layer due to a biological, chemical or physical interaction, which comprises:
 a sensor layer;
 a source of light, which irradiates the sensor layer, of wavelengths that include at least operating wavelengths, for which the sensor layer is transparent, at least, partially;
 a detector, which is placed on the pathway of the light reflected from the sensor layer or transmitted through the sensor layer, for measuring the light intensity of operational wavelengths in the spectrum of the received light;
 a block of result generation to generate information about the binding being detected on the basis of changes of the said spectrum, whose input is connected to the output of the detector,
 wherein:
 the thickness of the sensor layer is more than 10 micrometers and exceeds the
maximal operating wavelength by at least one order of magnitude,
 the detector is a matrix spectrometer.

2. An apparatus according to claim 1, wherein the source is a source of polychromatic light with continuous spectrum and coherence length that is less than double thickness of the sensor layer.

3. An apparatus according to claim 1, wherein the source is made on the basis of a light-emitting diode or superluminescent diode.

4. An apparatus according to claim 1, wherein at least part of the path from the source to the detector the light travels inside an optical fiber.

5. An apparatus according to claim 1, wherein the sensor layer is formed by a plate with two boundary surfaces not adjacent to any substrate.

6. An apparatus according to claim 5, wherein said substance is immobilized on a first boundary surface of the plate, said first boundary surface contacts the liquid or gaseous sample under test, which contains or presumably contains the biological or chemical component; a substance for adjusting of reflection coefficient is present on a second boundary surface so that both boundary surfaces have close reflection coefficients.

7. An apparatus according to claim 5, wherein both said boundary surfaces contact the liquid or gaseous sample under test, a substance capable to bind the said biological or chemical component being present on a first boundary surface of the plate.

8. An apparatus according to claim 1, wherein the sensor layer is formed by two boundary surfaces with a gap therebetween, the two boundary surfaces are formed by the solid optical materials.

9. An apparatus according to claim 1, wherein variation of optical thickness of the sensor layer within the irradiation spot by light that is directed from the source toward the sensor layer and further to the detector, does not exceed a fourth of wavelength for the smallest operating wavelength.

10. An apparatus according to claim 1, wherein the sensor layer consists of several spatially separated areas or comprises several spatially separated areas, which are irradiated by light from the source; the detector is made capable to measure the light intensity of operational wavelengths in the spectrum of the received light for each said area; the block of result generation is made capable to analyze changes of the said light intensity of operational wavelengths in the spectrum for each said area and generate information about the binding being detected on the basis of such changes.

11. An apparatus according to claim 10, wherein the sensor layer in each said area forms the bottom of a reaction cell, and the reaction cells produce an array, in particular, in the form of a microtiter plate or a biochip.

12. An apparatus according to claim 10, wherein an optical system to project light from the said areas to the detector is arranged on the pathway of light before the detector; the detector comprises a set of spectrometers, each spectrometer has output connected with the block of result generation.

13. An apparatus according to claim 10, wherein different substances capable to selectively bind various material components from a gaseous or liquid sample under test are arranged in the said areas of the sensor layer.

14. An apparatus according to claim 1, wherein light from the source, which irradiates the sensor layer is collimated, that is a source of collimated light is used as the light source or means for collimation of the light are introduced before the sensor layer.

15. An apparatus according to claim 1, wherein sensor layer is made of spatially separated pieces; said pieces contain different substances capable to selectively bind various material components; the block of result signal generation is made capable to analyze said change of the said spectrum for each said pieces and generate information about binding being detected on the basis of said change for each said pieces.

16. An apparatus according to claim 8, wherein said gap between two boundary surfaces is split by an insertion into a plurality of reaction cells including at least one reaction cell for use as a reference cell.

17. An apparatus for optical detection of binding of at least one material component to a substance located on a surface of or inside a sensor layer due to a biological, chemical or physical interaction, which comprises:
 a sensor layer;
 a source of light, which irradiates the sensor layer, of wavelengths that include at least operating wavelengths, for which the sensor layer is transparent, at least, partially;
 a detector, which is placed on the pathway of the light reflected from the sensor layer or transmitted through the sensor layer, for measuring the light intensity of operational wavelengths in the spectrum of the received light;
 a block of result generation to generate information about the binding being detected on the basis of changes of the said spectrum, whose input is connected to the output of the detector,
 wherein:
 the thickness of the sensor layer is more than 10 micrometers and exceeds the maximal operating wavelength by at least one order of magnitude,
 the detector is a spectrometer and wherein said spectrometer is made of a photodetector combined with a tunable monochromator or tunable spectral filter.

* * * * *